(12) United States Patent
Marban

(10) Patent No.: US 7,037,648 B1
(45) Date of Patent: May 2, 2006

(54) SOMATIC TRANSFER OF MODIFIED GENES TO PREDICT DRUG EFFECTS

(75) Inventor: Eduardo Marban, Lutherville, MD (US)

(73) Assignee: John Hopkins University, Baltimore, MD (US)

( * ) Notice: Subject to any disclaimer, the term of this patent is extended or adjusted under 35 U.S.C. 154(b) by 0 days.

(21) Appl. No.: 09/187,669

(22) Filed: Nov. 5, 1998

Related U.S. Application Data

(60) Provisional application No. 60/064,893, filed on Nov. 7, 1997.

(51) Int. Cl.
  *C12Q 1/68* (2006.01)
  *C12N 7/01* (2006.01)
  *C12N 15/00* (2006.01)
  *C12N 15/09* (2006.01)
  *C12N 15/63* (2006.01)

(52) U.S. Cl. .................. 435/6; 435/235.1; 435/320.1; 435/325; 435/455; 536/23.1; 536/23.4

(58) Field of Classification Search .............. 435/6, 435/235.1, 320.1, 29, 325, 455; 536/23.1, 536/23.4
  See application file for complete search history.

(56) References Cited

U.S. PATENT DOCUMENTS

| 5,436,128 | A |   | 7/1995 | Harpold et al. |
| 5,492,825 | A |   | 2/1996 | Jan et al. |
| 5,670,335 | A |   | 9/1997 | Jan et al. |
| 5,856,155 | A |   | 1/1999 | Li |
| 5,955,275 | A | * | 9/1999 | Kamb ............... 435/6 |

OTHER PUBLICATIONS

Balser, et al., *J. Clin. Invest.*, 98:12, 2874 (1996).
Balser, et al., *Biophys. J.*, 57: 433 (1990).
Barr, et al., *Gene Therapy*, 1: 51.
Barry et al., *Circ. Res.*, 77: 361 (1995) or p. 561.
Deal, K.D. et al., *Phys. Rev.*, 76: 49 (1996).
Dixon, et al., *Circ. Res.*, 75: 252 (1994).
Dixon, et al., *Circ. Res.*, 79: 659 (1996).
Donahue, et al., *Proc. Natl. Acad. Sci. USA* 94: 4664 (1997).
Fiset et al., *J. Physiology*, 500: 51.
Good et al., *Biophys. J.*, 70: 296 (1996).
Lee, et al., *J. Thorac. and Cardio. Surg.*, 111: 246 (1996).
Maletic-Savatic, et al., *J. Neurosci.*, 15: 3840 (1995).
Marshall, et al., *Neuron*, 14: 211 (1995).
Ribera, *J. of Neurosci.*, 16: 1123 (1996).
Rudy, *Neuroscience*, 25: 729 (1998).
Serodio, *J. Neurophys.*, 75: 2174 (1996).
Wagner, *Nature Medicine*, 1: 1116 (1995).
Gidh-Jian, et al., *Circulation Research*, vol. 79, No. 4, 660 (1996).
Kaab, et al., Circulation Research, vol. 78, No. 2, 262 (1996).

* cited by examiner

*Primary Examiner*—James Ketter
*Assistant Examiner*—Konstantina Katcheves
(74) *Attorney, Agent, or Firm*—Peter F. Corless; Stephana E. Patton; Edwards Angell Palmer & Dodge, LLP

(57) ABSTRACT

The present invention relates to somatic cell gene transfer methods for mimicking one or more effects of a drug candidate compound. In one aspect, the methods mimic the effect of a drug candidate compound with potential to potentiate or suppress activity of a selected target molecule. In another aspect, the methods provide means of identifying a molecular target for the drug candidate compound. The present methods have a variety of uses including providing identified molecular targets for use in drug screens.

32 Claims, 27 Drawing Sheets

| PROTEIN | DESCRIPTION | REFERENCE[1] | mRNA/gene Sequence[2] |
|---|---|---|---|
| VOLTAGE-GATED ION CHANNEL | | | |
| | K+ CHANNEL BETA 1A SUBUNIT | Hs.45090 | U33428<br>L39833<br>L47665 |
| SODIUM CHANNEL | VOLTAGE DEPENDANT SODIUM CHANNEL | | |
| CALCIUM CHANNEL | DIHYDROPRYRIDINE-SENSITIVE L-TYPE, CALCIUM CHANNEL BETA-1-B1 SUBUNIT | Hs.635 | L0611<br>M92392<br>M76560 |
| | DIHYDROPYRIDINE-SENSITIVE L-TYPE CALCIUM CHANNEL ALPHA-1 SUBUNIT (CACNLIA3) | Hs.1294 | L33798<br>U30707 |
| | NEURONAL DHP-SENSITIVE, VOLTAGE-DEPENDENT, CALCIUM CHANNEL ALPHA-2b SUBUNIT | Hs.1295 | M76559 |
| | DIHYDROPYRIDINE-SENSITIVE 1-TYPE, SKELETAL MUSCLE CALCIUM CHANNEL GAMMA SUBUNIT | Hs.1296 | L07738<br>Z19603 |
| | NEURONAL DHP-SENSITIVE, VOLTAGE-DEPENDENT, CALCIUM CHANNEL ALPHA-1D SUBUNIT | Hs.23838 | M76558<br>M83556<br>D43747 |
| | PUTATIVE CALCIUM INFLUX CHANNEL (htrp3) | H.24852 | U47050<br>Y13758 |
| | VOLTAGE-DEPENDENT CALCIUM CHANNEL ALPHA-1 E-3 | Hs.65441 | L29385<br>L29384<br>L27745 |
| | N-TYPE CALCIUM CHANNEL ALPHA- SUBUNIT | Hs.69949 | M94172<br>M94173 |
| | VOLTAGE-DEPENDENT L-TYPE Ca CHANNEL ALPHA 1 SUBUNIT | Hs.89925 | L29536<br>L29534<br>M92269 |

1 GENBANK REFERENCE DESIGNATION FOR PROTEIN. PROTEINS WITH NO DESIGNATION ARE REFERENCED IN THIS TEXT.
2 GENBANK mRNA OR GENE SEQUENCE REFERENCE DESIGNATION.

FIG. 1-A

| PROTEIN | DESCRIPTION | REFERENCE | mRNA/gene Sequence |
|---|---|---|---|
| LIGAND-GATED CHANNEL | GAMMA-AMINO BUTYRIC ACID (GABA) RECEPTOR NICTOTINIC ACETYLCHOLINE RECEPTOR | | |
| G-COUPLED RECEPTOR | P2Y6 RECEPTOR | Hs.16362 | AF007891 U52464 |
| | CHEMOKINE (C-C) RECEPTOR 7 | Hs.784 | L08177 |
| | HUMAN RPE-RETINAL G PROTEIN-COUPLED RECEPTOR | Hs.1544 | U14910 |
| | INWARDLY RECTIFYING POTASSIUM CHANNEL KIR3.2 | Hs.11173 | U52153 D87327 U24660 |
| | G PROTEIN-COUPLED RECEPTOR KINASE GRK4 | Hs.32859 | L03718 U33054 |
| | G PROTEIN-COUPLED INWARDLY RECTIFYING POTASSIUM CHANNEL Kir3.4 | Hs.37168 | U52154 |
| | G PROTEIN-ACTIVATED INWARDLY RECTIFYING POTASSIUM CHANNEL HGIRK1/Kir3.1 | Hs.37169 | U50964 |
| RECEPTOR-GATED CHANNEL | Fc FRAGMENT OF IgE, HIGH AFFINITY 1, RECEPTOR FOR; BETA POLYPEPTIDE | Hs.30 | M89796 |
| | INTERLEUKIN 2 RECEPTOR GAMMA CHAIN | Hs.84 | L19546 |
| | CHOLECYSTOKININ A RECEPTOR | Hs.129 | L13605 L19315 |
| | PERIPHERAL-TYPE BENZODIAZEPINE RECEPTOR | Hs.202 | M36035 |
| | CHOLECYSTOKININ B RECEPTOR | Hs.203 | L07746 L10822 |
| | GLUCAGON RECEPTOR | Hs.208 | L20316 |
| | SERINE/THREONINE-PROTEIN KINASE RECEPTOR R4 PRECURSOR | Hs.220 | L11695 |
| | FORMYL PEPTIDE RECEPTOR-LIKE 1 | Hs.251 | M84562 M88107 |
| | ADENOSINE RECEPTOR A3 | Hs.258 | L20463 L22607 |

FIG. 1-B

| PROTEIN | DESCRIPTION | REFERENCE | mRNA/gene Sequence |
|---|---|---|---|
| GROWTH FACTOR RECEPTOR | PLEIOTROPHIN (HEPARIN BINDING GROWTH FACTOR 8, NEURITE GROWTH-PROMOTING FACTOR 1) | Hs.44 | M57399 |
| | HEPATOCYTE GROWTH FACTOR ACTIVATOR PRECURSOR | Hs.104 | D14012 |
| | FIBROBLAST GROWTH FACTOR 9 (GLIA-ACTIVATING FACTOR) | Hs.111 | D14838 |
| | INSULIN-LIKE GROWTH FACTOR BINDING PROTEIN 2 | Hs.162 | M35410 |
| | HUMAN GROWTH FACTOR RECEPTOR TYROSINE KINASE (STK-1) | Hs.385 | U02687 |
| KINASE | PROTO-ONCOGENE C-COT (PROTEIN-SERINE/THREONINE KINASE) | Hs.248 | D14497 |
| | RECEPTOR PROTEIN-TYROSINE KINASE SKY | Hs.301 | U18934 D17517 |
| | CALCIUM/CALMODULIN-DEPENDENT PROTEIN KINASE IV | Hs.348 | D30742 L24959 |
| | CREATINE KINASE B | Hs.669 | M16451 L47647 |
| | V-raf MURINE SARCOMA VIRAL ONCOGENE HOMOLOG B1 | Hs.662 | M95712 |
| TRANSFERASE | GLUCOSAMINYL (N-acetyl) TRANSFERASE 1, CORE 2 | Hs.781 | M97347 L41415 |
| | GLUTATHIONE S-TRANSFERASE, MICROSOMAL | Hs.790 | J03746 |
| | UDP GLUCOSYLTRANSFERASE 8 (UDP-GALACTOSE CERAMIDE GALACTOSYLTRANSFERASE) | Hs.57700 | U30930 U62899 |
| ISOMERASE | PEPTIDYLPROLYL ISOMERASE B (CYCLOPHILIN B) | Hs.699 | |
| | 3-BETA HYDROXY-5-ENE STEROID DEHYDROGENASE TYPE II | Hs.825 | M67466 N77144 |
| | GLUCOSE PHOSPHATE ISOMERASE | Hs.944 | K03515 |
| | HYDROXY-DELTA-5-STEROID DEHYDROGENASE, 3-BETA- AND STEROID DELTA-ISOMERASE 1 | Hs.38586 | M27137 M38180 |
| PROTEASE | 26S PROTEASE REGULATORY SUBUNIT 4 | Hs.548 | L02426 |
| | HEPSIN | Hs.823 | M18930 |
| | GRANZYME B PRECURSOR | Hs.1051 | M17016 |
| DEHYDROGENASE | GLYCINE CLEAVAGE SYSTEM PROTEIN P (GLYCINE DECARBOXYLASE) | Hs.27 | M64590 |
| | 17 BETA HYDROXYSTEROID DEHYDROGENASE, TYPE 2 | Hs.181 | L11708 |

FIG. 1-C

| PROTEIN | DESCRIPTION | REFERENCE | mRNA/gene Sequence |
|---|---|---|---|
| DEHYDROGENASE | XANTHINE DEHYDROGENASE | Hs.250 | D11456 |
| | ALCOHOL DEHYDROGENASE 7 SIGMA SUBUNIT (CLASS IV) | Hs.389 | U09623 U07821 |
| | SUCCINATE DEHYDROGENASE 2, FLAVOPROTEIN (Fp) SUBUNIT | Hs.469 | D30648 L21936 |
| SYTHETASE | LONG CHAIN FATTY ACID ACYL-coA LIGASE | Hs.34 | L09229 |
| | FOLYLPOLYGLUTAMATE SYNTHETASE | Hs.754 | M98045 |
| | GLUTAMATE-CYSTEINE LIGASE (GAMMA-GLUTAMYLCYSTEINE SYNTHETASE), CATALYTIC | Hs.1673 | M90656 |
| | HYDROXYMETHYLBILANE SYNTHASE | Hs.82609 | M95623 |
| DEAMINASE | DIPEPTIDYLPEPTIDASE IV (CD26, ADENOSINE DEAMINASE COMPLEXING PROTEIN 2) | Hs.44926 | M80536 |
| | DEOXYCYTIDYLATE DEAMINASE | Hs.76894 | L12136 |
| | AMP DEAMINASE 2 | Hs.82927 | U16270 |
| | ADENOSINE MONOPHOSPHATE DEAMINASE (ISOFORM E) | Hs.83918 | M84721 |
| ONCOGENE | V-crk AVIAN SARCOMA VIRUS CT10 ONCOGENE HOMOLOG | Hs.16 | D10656 |
| | THYROID HORMONE RECEPTOR, ALPHA (AVIAN ERYTHROBLASTIC LEUKEMIA VIRAL (v-erb-a) ONCOGENE HOMOLOG) | Hs.724 | M24899 |
| | FRIEND LEUKEMIA VIRUS INTEGRATION I | Hs.736 | M98833 |
| | RAP1A, MEMBER OF RAS ONCOGENE FAMILY | Hs.865 | M22995 |
| | THROMBOPOIETIN (MYELOPROLIFERATIVE LEUKEMIA VIRUS ONCOGENE LIGAND, MEGAKARYOCYTE GROWTH AND DEVELOPMENT FACTOR | Hs.1166 | L36051 |
| | FIBROBLAST GROWTH FACTOR 4 (HEPARIN SECRETORY TRANSFORMING PROTEIN 1, KAPOSI SARCOMA ONCOGENE) | Hs.1755 | J02986 M17446 |
| | V-erb-a AVIAN ERYTHROBLASTIC LEUKEMIA VIRAL ONCOGENE HOMOLOG-LIKE 4 | Hs.1939 | L07868 |
| FOS | P55-c-fos PROTO-ONCOGENE PROTEIN | Hs.25647 | V01512 |
| JUN | C-jun PROTO ONCOGENE (JUN) | Hs.78465 | J04111 |
| | Jun B PROTO-ONCOGENE | Hs.89792 | M29039 |

FIG. 1-D

| PROTEIN | DESCRIPTION | REFERENCE | mRNA/gene Sequence |
|---|---|---|---|
| Myc | V-myc AVIAN MYELOCYTOMATOSIS VIRAL ONCOGENE HOMOLOG | Hs.79070 | K02276 M20605 |
| | MAD PROTEIN (MAX-BINDING PROTEIN) | Hs.82231 | L06895 |
| Myb | PROTO-ONCOGENE c-myb (ALTERNATIVE PRODUCTS) | Hs.1334 | M15024 |
| Abl | Arg PROTEIN TYROSINE KINASE-BINDING PROTEIN | Hs.86870 | U31089 |
| Scr | MEGAKARYOCYTE-ASSOCIATED TYROSINE KINASE | Hs.274 | L18974 |
| | FYN ONCOGENE RELATED TO SRC, FGR, YES | Hs.75390 | M14676 M14333 |
| Ras | GTPase-ACTIVATING PROTEIN ras p21 (RASA) | Hs.758 | M23612 M23379 |
| CELL DEATH | DEFENDER AGAINST CELL DEATH | Hs.82890 | D15057 |
| | POSITIVE REGULATOR OF PROGRAMMED CELL DEATH ICH-IL, (Ich-1) | Hs.108131 | U13021 |

FIG. 1-E

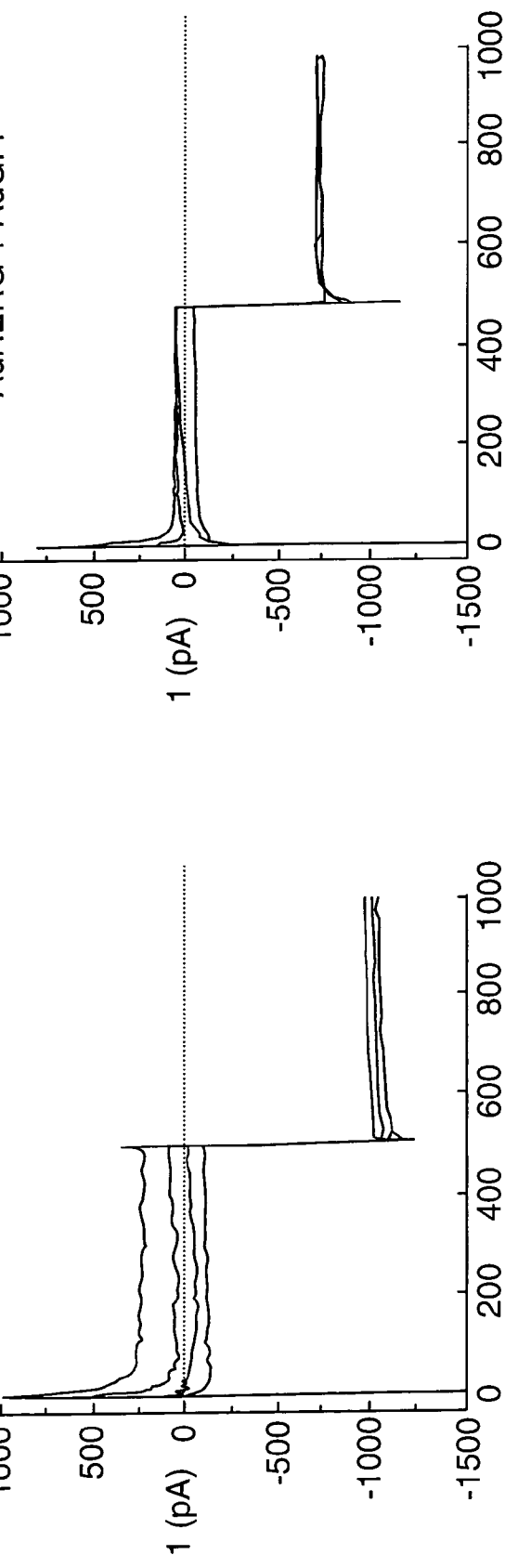
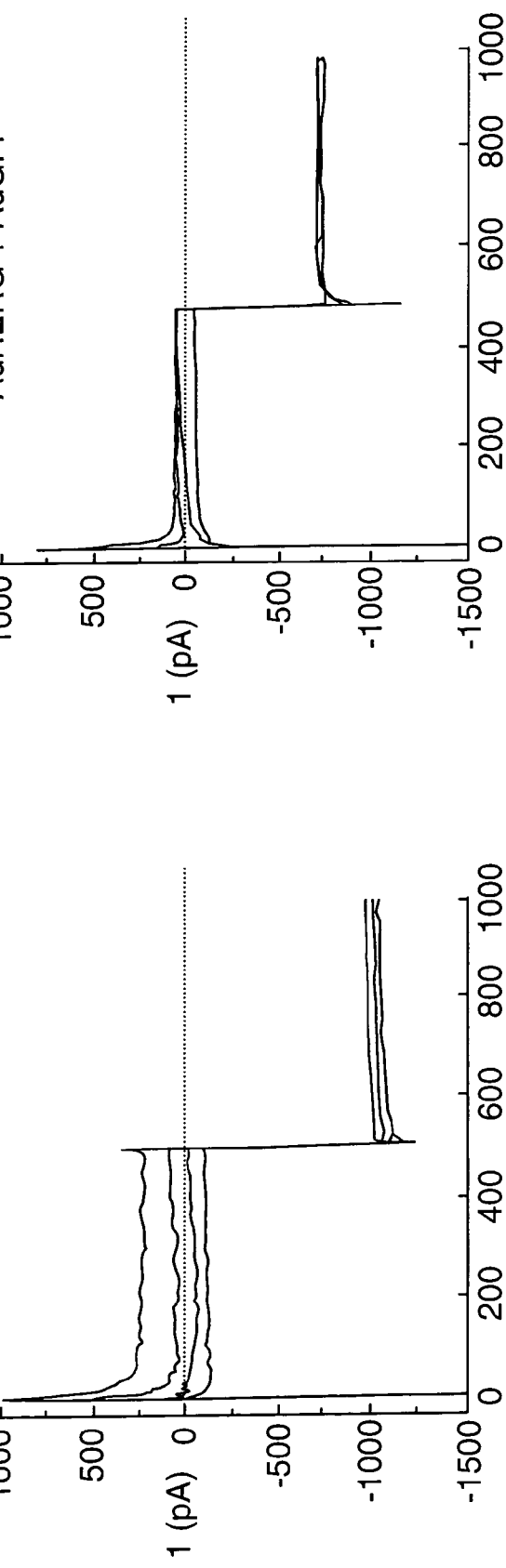
FIG. 2D
FIG. 2C

ALIGNMENT

| | |
|---|---|
| KV4.2 FL | MAAGVAAWLPFARAAAIGWMPVASGPMPAPPRQERKRTQDALIVLNVSGTRFQTWQDTLE 60 |
| KV4.2 ST | MAAGVAAWLPFARAAAIGWMPVASGPMPAPPRQERKRTQDALIVLNVSGTRFQTWQDTLE 60 |
| KV4.2 FL | RYPDTLLGSSERDFFYHPETQQYFFDRDPDIFRHILNFYRTGKLHYPRHECISAYDEELA 120 |
| KV4.2 ST | RYPDTLLGSSERDFFYHPETQQYFFDRDPDIFRHILNFYRTGKLHYPRHECISAYDEELA 120 |
| KV4.2 FL | FFGLIPEIIGDCCYEEYKDRRRENAERLQDDADTDNTGESALPTMTARQRVWRAFENPHT 180 |
| KV4.2 ST | FFGLIPEIIGDCCYEEYKDRRRENAERLQDDADTDNTGESALPTMTARQRVWRAFENPHT 180 |
| KV4.2 FL | STMALVFYYVTGFFIAVSVIANVVETvpcgsspghikelpcgeryavaffcldtacvmif 240 |
| KV4.2 ST | STMALVFYYVTGFFIAVSVIANVVETgsrhdkih------------------------- 214 |
| KV4.2 FL | tveyllrlaaapsryryfvrsvmsiidvvailpyyiglvmtdnedvsgafvtlrvfrvfri 300 |
| KV4.2 ST | ------------------------------------------------------------ 214 |
| KV4.2 FL | fkfsrhsgglrilgytlkscaselgfllfsltmaiiifatvmfyaekgssaskftsipaa 360 |
| KV4.2 ST | ------------------------------------------------------------ 214 |
| KV4.2 FL | fwytivtmttlgygdmvpktiagkifgsicslsgvlvialpvpvivsnfsriyhqnqrad 420 |
| KV4.2 ST | ------------------------------------------------------------ 214 |
| KV4.2 FL | krraqkkarlariraaksgsanaymqskrngllsnqlqssedepafvsksgssfetqhhh 480 |
| KV4.2 ST | ------------------------------------------------------------ 214 |
| KV4.2 FL | llhclektnhefvdeqvfeescmevatvnrpsshspslssqqgvtstccsrrhkktfri 540 |
| KV4.2 ST | ------------------------------------------------------------ 214 |

FIG. 3B

KV4.2 FL   pnanvsgshrgsvqelstiqircvertplsnsrsslnakmeecvklnceqpyvttaiisi   600
KV4.2 ST   ------------------------------------------------------------   214

KV4.2 FL   ptppvttpegddrpespeysggnivrvsal   630
KV4.2 ST   ------------------------------   214

FIG. 3C

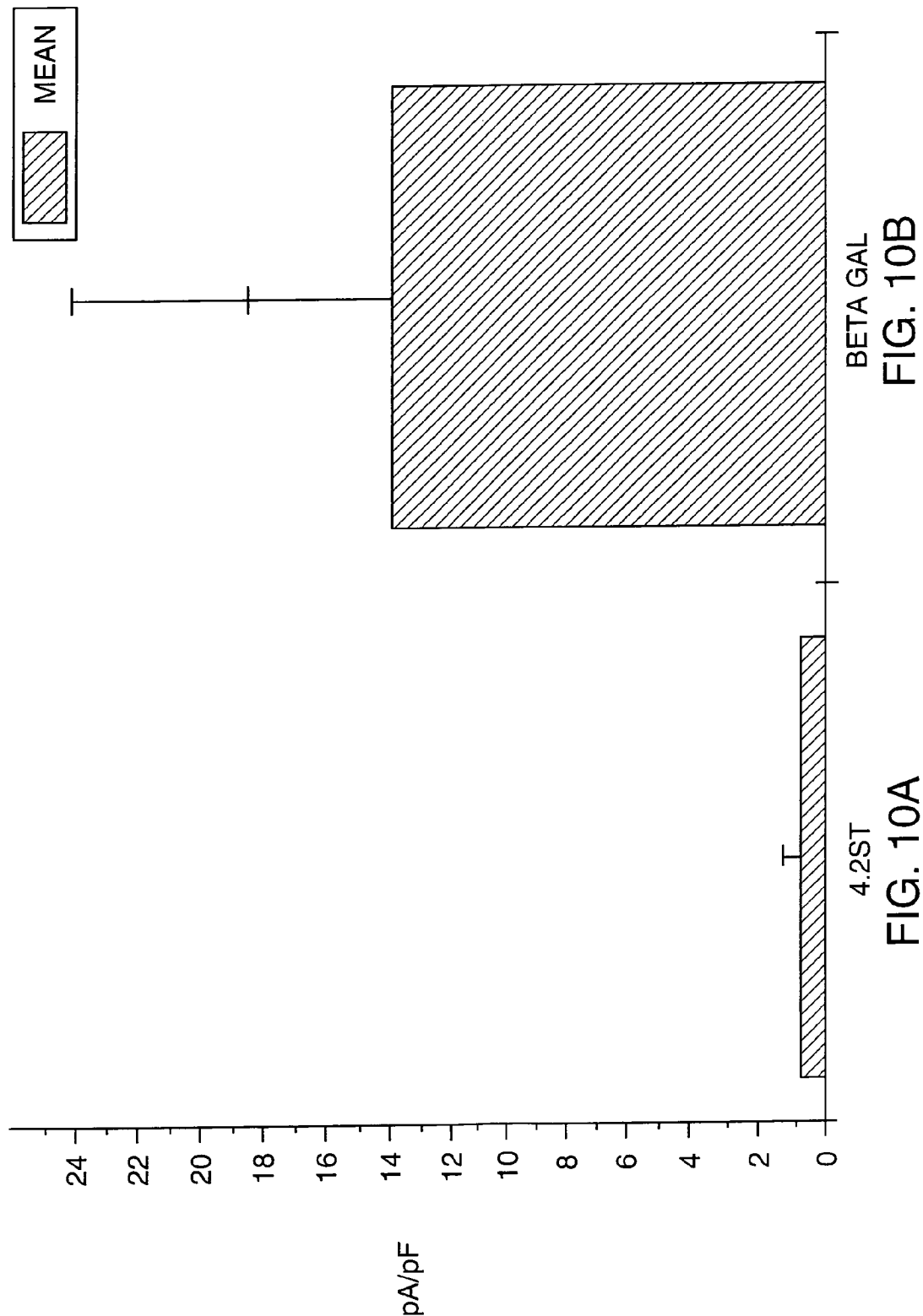

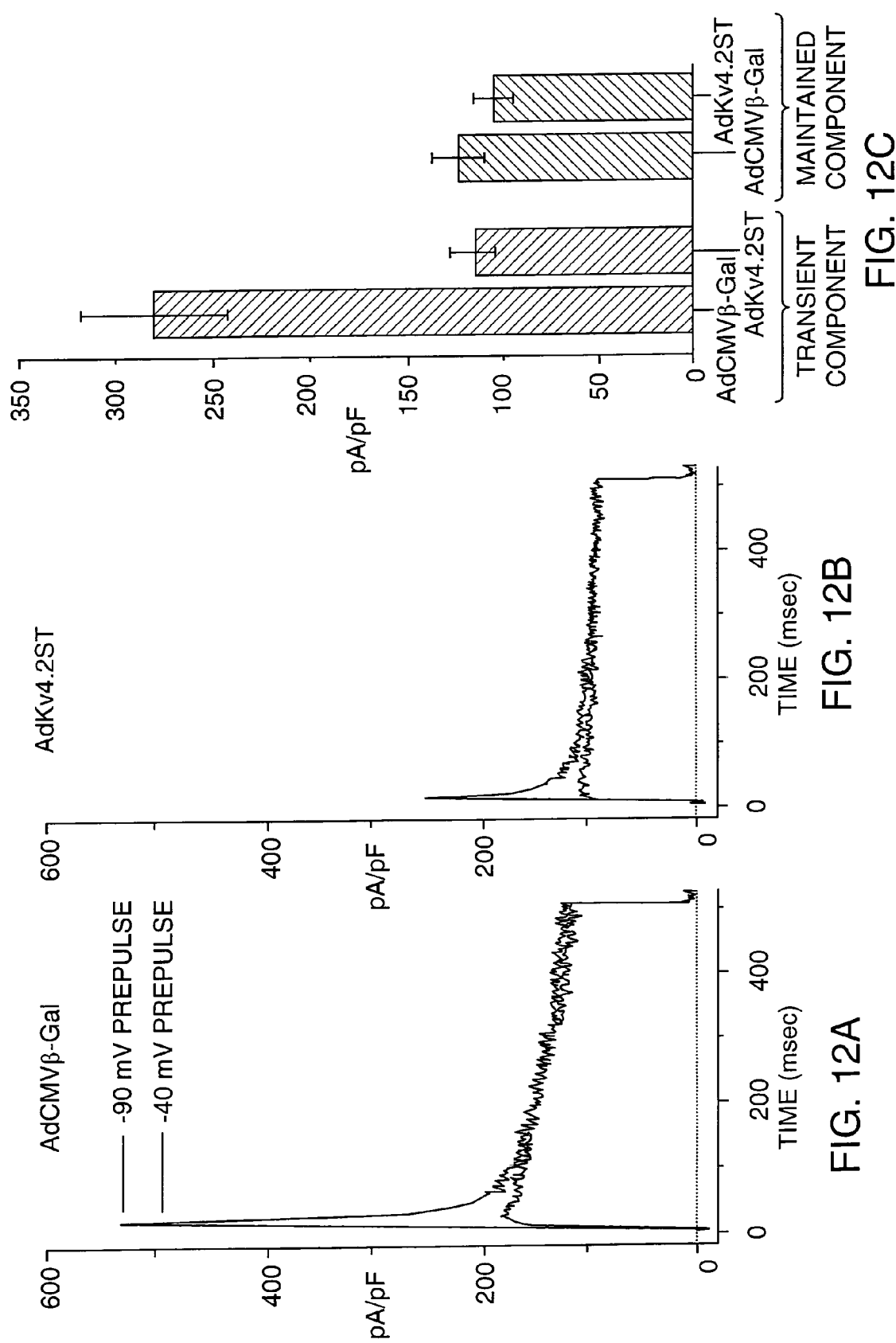

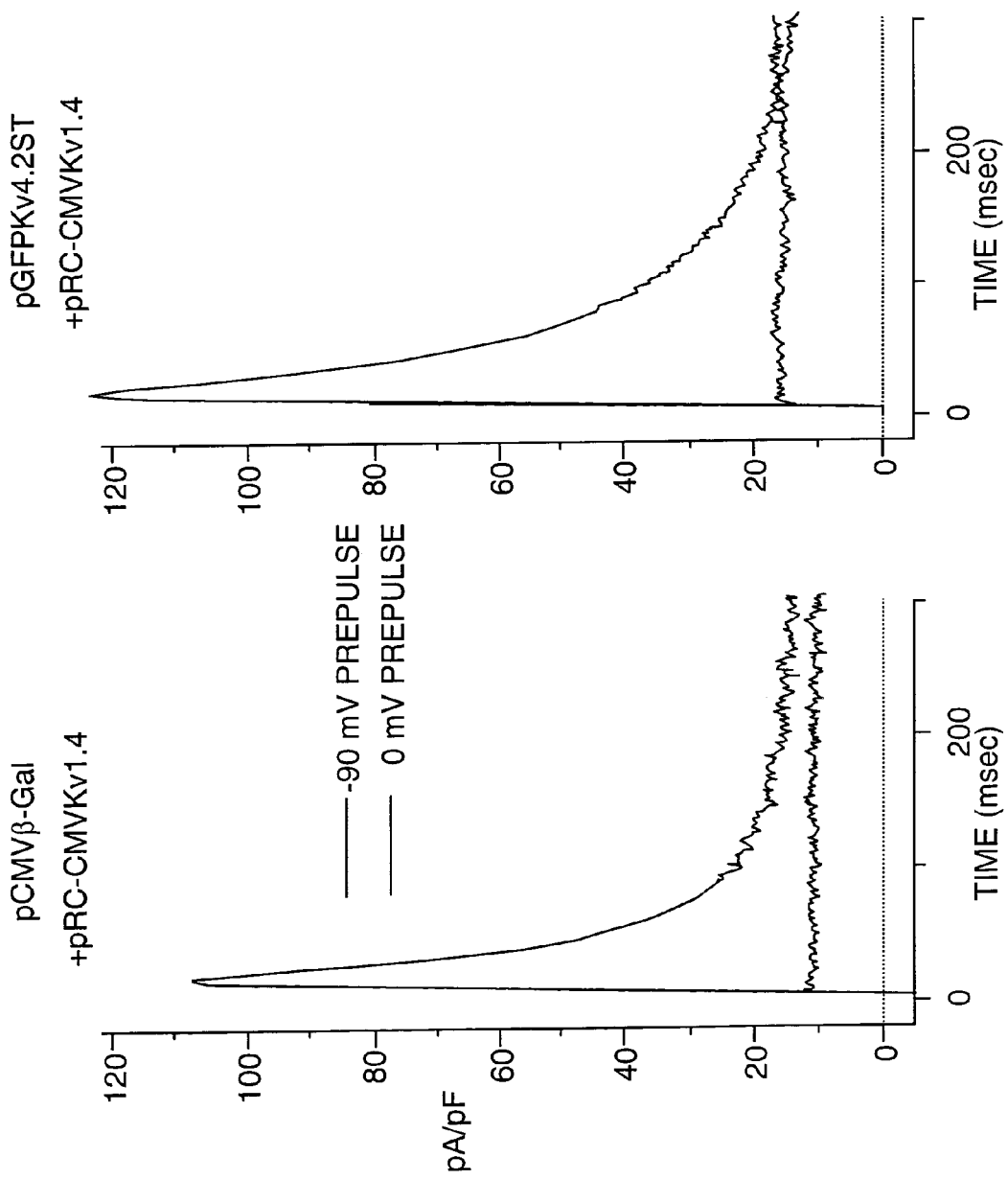
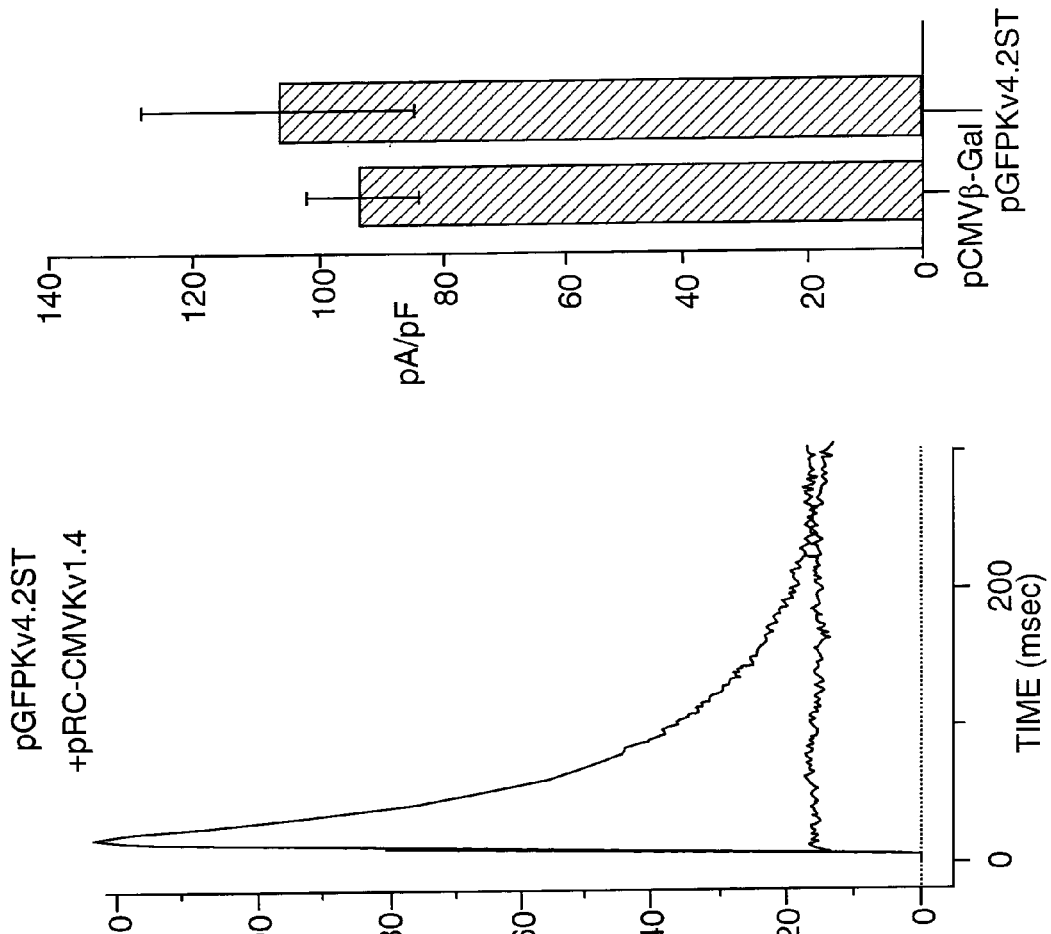
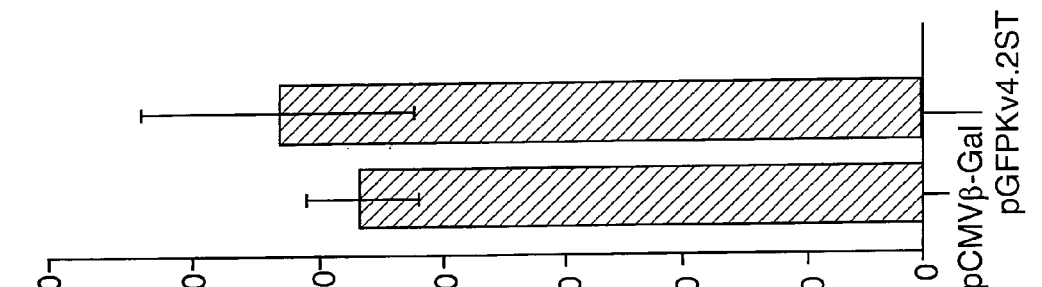
FIG. 14A
FIG. 14B
FIG. 14C

SOMATIC TRANSFER OF MODIFIED GENES TO PREDICT DRUG EFFECTS

The present application is a continuation of co-pending U.S. provisional application Ser. No. 60/064,893, filed Nov. 7, 1997, which is incorporated by reference herein in its entirety.

BACKGROUND OF THE INVENTION

1. Field of the Invention

The present invention relates to somatic cell gene transfer methods for mimicking one or more effects of a drug candidate compound. In one aspect, the methods mimic the effect of a drug candidate compound with potential to potentiate or suppress activity of a selected target molecule. In another aspect, the methods provide means of identifying a molecular target for the drug candidate compound. The present methods have a variety of uses including providing identified molecular targets for use in drug screens.

2. Background

Eukaryotic organisms include a variety of cells, tissues and organs that react to stimuli. Cell pathways have evolved to react to the stimuli. The cell pathways generally include molecules such as receptors, pore- or channel-forming proteins, enzymes, growth factors, differentiation factors, messenger molecules, immunocompatibility factors and certain structural molecules. See generally Alberts, B. et al. (1989) in *The Molecular Biology of the Cell* 2$^{nd}$ ed. Garland Publishing, Inc. New York; and Kandel, E. R. et al. (1991) in *Principles of Neuroscience* 3$^{rd}$ ed. Appleton & Lange, Norwalk, Conn.

In particular, specified cell pathways include complexes of ion channel proteins that propagate charge between certain electrically responsive cells. See e.g., Hille, B. (1991) *Ionic Channels of Excitable Membranes,* 2 ed. Sunderland, Mass. Sinauer.

The cell pathways play a major role in the function of eukaryotes. Accordingly, there have been substantial efforts toward identifying drugs with therapeutic capacity to modulate the cell pathways in a predictable manner.

Several traditional approaches have been developed to detect drugs with therapeutic capacity to modulate the cell pathways.

For example, "natural products testing" is one such approach. In a typical approach, material is obtained from a biological source and then screened for a pre-determined activity. Positive results are usually followed by purification of the material from the biological source and identification of the molecule(s) responsible for the activity. See e.g., Hardman et al. (1996) eds. in *Pharmacological Basis of Therapeutics* 9$^{th}$ ed. McGraw-Hill.

Other approaches encompass what is sometimes referred to as "synthetic chemical testing". In this approach, a promising lead compound is synthesized and optionally derivatized by specified chemical manipulations. Typically, there exists substantial knowledge with respect to the structure and function of that lead compound as well as the manipulations necessary to develop a drug candidate compound from the lead compound. See e.g., Hardman et al. supra.

However, such traditional approaches for developing drugs have recognized shortcomings.

For example, natural products testing can require access to a large variety of organisms many of which may be rare or produce drug candidate compounds in limiting quantities. Labor and time investments are typically substantial. In most cases, there is incomplete knowledge as to the structure and function of the compounds. Even less is usually known about the molecular targets of such compounds.

Approaches relying on synthetic chemical testing have suffered from related shortcomings. For example, chemical manipulations required to make a drug candidate compound can be labor intensive and require several years of research effort. In many instances, development of a promising compound has proceeded without adequate knowledge of the molecular target(s) of that compound.

More generally, the traditional approaches have been hampered by inadequate knowledge of the molecular targets of many drug candidate compounds. That lack of knowledge can negatively impact efforts to identify and develop the compounds. By focussing on the target molecule of the compound, the traditional approaches may miss opportunities to detect a variety of promising compounds.

In particular, a promising drug candidate compound may go undetected in a traditional approach if that compound cannot interface with a molecular target. For example, a compound with unsuitable solubility or stability may be discarded in a traditional screen even though that compound can potentiate or suppress activity of a key target molecule such as a protein.

There have been recent attempts to circumvent or at least reduce the need to identify the molecular targets of drug candidate compounds. In general, screens have been implemented that substantially increase the diversity of known lead compounds. The objective has been to increase the number of lead compounds in the hope of identifying a compound of interest.

For example, combinatorial chemistry is one approach for substantially increasing the diversity of lead compounds. The technique is premised on the general assumption that production of large libraries of lead compounds and particularly lead compound derivatives, will provide a pool from which can be selected a significant number of drug candidate compounds. See e.g., Brenner et al. (1992) *PNAS (USA)* 89: 5381 Nielsen et al. (1993) *J. Am. Chem. Soc.* 115: 9812 and references cited therein.

More recently, there have been efforts to integrate computer-assisted modeling techniques and combinatorial chemistry into a unified screening approach for detecting drug candidate compounds. The approach is sometimes referred to as "targeted diversity" or "rational drug design".

However, combinatorial chemistry and targeted diversity suffer from significant drawbacks. For example, although these approaches have potential to increase pools of drug candidate compounds, implementation is not always cost and time effective. For example, these screening techniques are often negatively impacted by a lack of understanding of molecular targets of the lead compounds.

Accordingly, in many instances the molecular targets of the drug candidate compounds are unknown, thereby potentially stalling development of future compounds. Efforts to improve existing compounds may suffer a related fate.

There has been substantial research efforts toward identifying ion channels such as potassium channels. The ion channels represent a highly diverse family of proteins of particular pharmacological interest. The proteins are known to form multimeric membrane complexes. See e.g., Deal, K. D. et al. (1996) *Phys. Rev.* 76: 49; Rudy, B. (1998) *Neuroscience* 25: 729.

Specifically, certain ion channel proteins have been reported to be involved in human diseases such as epilepsy, heart failure and inherited long QT syndrome. See e.g., Bassett, A. L., et al. (1994) *Circ Res* 75:296; Tsaur, M. L., et al. (1992) *Neuron* 8: 1055; Kaab, S., et al. (1996) *Circ Res* 78 (2), 262–73; and Good, T. A., et al. (1996) *Biophys. Journal* 70: 296.

Selective gene suppression is an approach for understanding protein function. For example, antisense and dominant negative methodologies have been used to manipulate function of certain ion channel proteins. See e.g., Wagner, R. W. (1995) *Nature Medicine* 1: 1116.

It thus would be useful to have assays that mimic the effects of drug candidate compounds and particularly those compounds with capacity to potentiate or suppress activity of a specified target molecule. It would be particularly desirable to have in vitro assays that can identify the target molecule without complete knowledge of the compound. It would be further desirable to have in vitro assays that effectively mimic diseases or disorders impacted by the target molecule and the compound.

SUMMARY OF THE INVENTION

The present invention provides novel somatic gene transfer methods for mimicking one or more effects of a drug candidate compound. Generally stated, the methods are in vitro assays that modulate expression of a selected target molecule and analyze consequences of that modulation to evaluate effects of the drug candidate compound. Preferred methods of the invention positively identify target molecules for drug candidate compounds with capacity to potentiate or suppress activity of that target molecule. Particularly preferred methods mimic human diseases or disorders impacted by the target molecule and the drug candidate compound.

Significantly, the present methods are complementary to traditional drug screening approaches and can enhance those approaches by providing identified target molecules, particularly in the absence of lead compounds.

Preferred methods of the present invention are in vitro assays that involve somatic cell gene transfer and include one or more of the following steps 1) through 4):

1) culturing in medium a population of selected somatic cells, a tissue or an organ capable of expressing a recombinant nucleic acid segment such as a protein, preferably a native protein;
2) modifying the nucleic acid segment sufficient to modulate the result of expression of the protein in the cells, tissue or organ;
3) introducing the modified nucleic acid segment into the cells, tissue or organ under somatic cell gene transfer conditions sufficient to express a modified protein; and
4) analyzing the result of expression of the modified protein to mimic (or predict) the effect of the drug candidate compound in the cells, tissue or organ.

The result of expression of the modified protein mimics one or more effects of the drug candidate compound, particularly those compounds with capacity to potentiate or suppress activity of the protein expressed by the nucleic acid segment.

Particularly, step 4) above can encompass correlating the result of expression of the modified protein to the result of expression of a corresponding native protein. Sometimes, that native protein will be referred to herein as a "full-length" "normal" or "wild-type" to denote natural occurrence of that native protein in the selected somatic cell, tissue or organ. Analysis of the result of expression of the native protein can be conducted in a parallel (i.e. control) assay that includes one or more of the steps 1) through 4) above except that the protein is not modified.

A modified protein of the present invention typically exhibits at least 10 percent or greater activity relative to the full-length protein; more preferably at least 20 percent or greater activity; and still more preferably at least about 30, 40, 50, 60, 70, 80, 100, 150, or 200 percent or greater activity relative to the full-length protein. Such activity of the modified protein will be considered indicative of mimicking activity of a drug candidate compound. Particularly preferred are those activities that point to drug candidate compounds which would potentiate (i.e. greater than 100%) or suppress (i.e. less than 100%) activity of the corresponding native protein in the selected cell, tissue or organ.

Thus, "mimicking" as the term is used herein is evidenced by an activity of the modified protein in the above generally described assay when compared to the native protein (i.e. control). That activity typically manifests a detectable phenotype in the selected somatic cell, tissue or organ. For example, the phenotype can be a morphological alteration or a functional change that can be assayed (and quantitated if desired) by a method known in the art including those specified below.

Significantly, the change in activity of the modified protein can be impacted by several factors including 1) the somatic cell, tissue or organ selected, 2) the target molecule selected and particularly the specificity the drug candidate compound would have for that molecule, and 3) the potency of the drug candidate compound would have in that selected cell, tissue or organ.

More particularly, by the term "mimic" or "predict" as those terms relate to invention, is meant an identified consequence the drug candidate compound would have in the selected cell, tissue or organ. That consequence is manifested by expression of the modified protein when that expression is compared to its native counterpart. Thus, by mimicking the effect of a drug candidate compound, particularly compounds that would potentiate or suppress activity of the selected target molecule, the present methods can be performed without knowledge the drug candidate compound.

For example, the present invention does not require knowledge of the structure or synthesis of the drug candidate compound in order to identify the molecular target of that compound.

Molecular targets and particularly proteins targets such as ion channels identified in accord with the invention will generally find important use, e.g., as important starting reagents in traditional drug discovery screens. Such targets will be particularly useful in those traditional drug screens for which there is no reliable lead compound.

Reference herein to a "standard in vitro assay" in accord with the invention refers to the above protocol of steps 1) through 4).

A nucleic acid segment suitable for use with the present invention can be nearly any nucleic acid segment that encodes a protein such as a cDNA or genomic sequence. Preferably the encoded protein is full-length although in some instances the nucleic acid segment may encode a protein fragment.

It is particularly preferred that the nucleic acid segment be compatible with conventional somatic cell gene transfer techniques such as described herein.

Somatic cell gene transfer techniques in accord with the invention generally include standard techniques for controllably expressing an introduced gene into non-germ line cells (i.e. non-sperm or egg cells). For example, in one approach, what is often referred to as "ex vivo" methods are used to remove somatic cells from a host organism (sometimes known as primary cells). The cells are then used as recipient cells for transfer of a gene of interest into the cells. Subsequently, the genetically modified cells can be implanted back into the recipient host organism. Particularly, such techniques can be use for study of cells ex vivo, e.g., in the phenotypic characterization of ion channel protein "knock-outs".

In what is sometimes referred to as an "in vivo" somatic cell gene transfer technique, a desired gene is introduced into cells of a host organism without removing those cells from the host organism.

Preferred methods of the invention typically employ ex vivo somatic cell gene transfer or a related ex vivo technique to introduce a nucleic acid segment of interest into selected somatic cells, tissues or organs. Typically, use of that technique is sufficient to express the protein encoded by nucleic acid segment in quantities detectable at the RNA or protein level.

The present methods can be performed with nearly any cell, tissue or organ that is compatible with a recognized somatic cell gene transfer techniques and particularly those techniques that include ex vivo manipulations. Exemplary cells include primary or native cells obtained directly from a host animal of interest such as a mammal and particularly a primate such as a human. More particularly, the cells are somatic in the sense that the cells are not germ-line cells and can include such cells as those obtained from the nervous or circulatory system, the immune, reproductive, digestive, respiratory or lymphatic system, the hepatic system, or the skin. Particular examples include cells isolated from heart tissue. As noted, groups of such cells may also be used in the form of selected tissues or organs.

More specifically, a somatic cell, tissue or organ of interest is compatible with a recognized somatic cell gene transfer technique and particularly the ex vivo technique outlined above, if at least 20%, preferably at least 50%, 60%, 70%, and more preferably at least 95% or more of the total number of cells are transformed by use of technique. Methods for determining the percentage of cells transformed by somatic cell gene transfer technique are known in the field and include analyzing expression of a detectable reporter protein (e.g., β-galactosidase, luciferase or the like) by well known immunological methods such as those employing monoclonal antibodies and/or fluorescence microscopy.

It has been reported that certain somatic cell gene transfer techniques and particularly ex vivo techniques rely on viral delivery of a desired nucleic acid segment. Thus, a nucleic acid segment for use in accord with the present invention must be compatible with the chosen viral delivery system. As a specific example, for somatic cell gene transfer delivery systems using viral vectors and particularly adenovirus or adenovirus-based vectors, the nucleic acid segment will typically be ligated into a suitable site in the vector which facilitates expression in the selected cell, tissue or organ. It is preferred that the size of the nucleic acid segment will not increase the size of that vector by more than about 1% to 10%, preferably no more than about 1% to 5%, and more preferably no more than about 1%, 2%, 3%, or 4%.

A large variety of encoded proteins are compatible with the present invention. The function of the protein can be unknown in which case the phenotypic consequences of expressing the protein can be detected by procedures known in the field. Alternatively, the function of the protein can be known or suspected in which case the result of expressing the wild-type or modified protein can be readily tested by specified assays such as those described below.

Thus, by the term "result" or "consequence" of expression is meant a phenotype that is manifested in the selected cells, tissue or organ by expression of the full-length or modified protein. The result of expression can be detected by one or a combination of different strategies such as those described below.

Preferred time frames for assaying the result of expression of a protein will vary with the protein, cell, tissue or organ chosen. However it is generally preferred that the result of expression be manifested within about 10 minutes to 72 hours or more up to about 1 to 2 weeks, preferably within about 30 minutes to 48 hours, more preferably within about 1 to 12 hours and even more preferably within about 1 to 2 hours following somatic gene transfer of the nucleic acid segment into the selected cells, tissues or organs.

For example, many phenotypic manifestations such as specified morphology changes and functional changes fall within those time frames when assayed by most somatic cell gene transfer techniques. Such phenotypes include, but are not limited to, propagation of an electrical charge, growth, blebbing or budding, pycnotic transformation, kinesis, cell death, differentiation, replication, transcription, translation, protein processing, adhesion, oncogenic transformation, enzymatic catalysis, protein modification, etc.

As noted, the present invention is compatible with use of a large variety of nucleic acid sequences and particularly cDNA sequences. A preferred cDNA encodes a protein that typically includes a signal sequence, a mature protein sequence (sometimes referred to as a complete coding sequence or "cds"); and a poly-adenylation sequence. In particular, the cds will include a single open-reading frame (ORF) and will usually also include one or more protein "motifs" e.g., one or more transmembrane domains, extracellular and intracellular domains, ligand binding domains, and/or protein modification site such as those involved with glycosylation, phosphorylation, or protein processing site.

In general, the cDNA or other suitable nucleic acid sequence of interest is inserted into a suitable somatic cell transformation vector such as those specific adenovirus vectors described below.

Significantly, most cds sequences and protein motifs are readily detectable by a variety of well-known computer-assisted programs. In particular, many of the programs can establish relationship between an unknown protein and a known protein. Thus, for a nucleic acid segment and particularly a cDNA sequence encoding a protein of unknown function, a function can often be assigned, e.g., by computer-assisted programs such as those specifically identified below.

As noted above, a full-length protein encoded by a cDNA will sometimes be referred to as a normal, or wild-type protein to denote natural occurrence of that protein in a subject, particularly a mammal and more particularly a primate such as a human. In contrast, a protein "modified" in accordance with the invention does not usually occur in that subject and must be made by recombinant manipulations described herein.

More specifically, a protein "modified" in accordance with the invention can, e.g., be overexpressed relative to the wild-type protein.

For example, one way to overexpress the protein is to operably link a cDNA encoding that protein to a strong viral promoter such as the cytomeglovirus (CMV) or rous sarcoma (RSV) viral promoter. Following somatic gene transfer in a suitable transformation vector, that protein is typically overexpressed relative to the native protein.

As will be explained more fully below, a protein modified in accord with the invention may also include one or more contiguous or non-contiguous amino acid additions, substitutions, or deletions relative to the full-length protein sequence.

As will also be explained, certain modifications of proteins in accord with the invention will be genetically dominant so as to inhibit function of other proteins particularly those proteins capable of forming binding complexes with the wild-type protein. Sometimes those modified proteins will be referred to as "dominant negative" proteins.

It will be appreciated by those of skill in the field that a protein in accord with the invention can be essentially full-length. That is, the protein may not have all the components of a full-length sequence. For example, the protein may include a complete or nearly complete cds but lack a complete signal or poly-adenylation sequence. It is preferred that a nucleic acid and particularly a cDNA encoding a protein include at least a complete cds. That cds is preferably capable of encoding a protein exhibiting a molecular weight of between about 0.5 to 70, preferably between about 5 and 60, and more preferably about 15, 20, 25, 30, 35, 40 or 50 kD. That molecular weight can be readily determined by suitable computer-assisted programs or by SDS-PAGE gel electrophoresis.

Although generally not preferred, the nucleic acid segment can be a genomic sequence or fragment thereof comprising one or more exon sequences. In this instance it is preferred that the cell, tissue or organ selected for performing somatic cell gene transfer be capable of correctly splicing any exon sequences so that a full-length or modified protein can be expressed.

The nucleic acid segment and particularly the cDNA encoding the full-length protein can be modified by conventional recombinant approaches to modulate expression of that protein in the selected cells, tissues or organs.

More specifically, the nucleic acid segment can be modified by recombinant methods that can add, substitute or delete one or more contiguous or non-contiguous amino acids from that encoded protein. In general, the type of modification conducted will relate to the result of expression desired.

For example, a cDNA encoding a protein of interest such as an ion channel can be modified so as overexpress that protein relative to expression of the full-length protein (i.e. control assay). Typically, the modified protein will exhibit at least 10 percent or greater overexpression relative to the full-length protein; more preferably at least 20 percent or greater; and still more preferably at least about 30, 40, 50, 60, 70, 80, 100, 150, or 200 percent or greater overexpression relative to the control assay.

As noted above, further contemplated modifications to a nucleic acid segment and particularly a cDNA are those which create dominant negative proteins.

In general, a variety of dominant negative proteins can be made by methods known in the field. For example, ion channel proteins are recognized as one protein family for which dominant negative proteins can be readily made, e.g., by removing selected transmembrane domains. In most cases, the function of the ion channel binding complex is substantially reduced or eliminated by interaction of a dominant negative ion channel protein.

Several specific strategies have been developed to make dominant negative proteins. Exemplary of such strategies include oligonucleotide directed and targeted deletion of cDNA sequence encoding the desired protein. Less preferred methods include nucleolytic digestion or chemical mutagenesis of the cDNA.

It is stressed that creation of a dominant negative protein is not synonymous with other conventional methods of gene manipulation such as gene deletion and antisense RNA. What is meant by "dominant negative" is specifically what is sometimes referred to as a "poison pill" which can be driven (i.e. expressed) by an appropriate DNA construct to produce a dominant negative protein which has capacity to inactivate an endogenous protein.

For example, in one approach, a cDNA encoding a protein comprising one or more transmembrane domains is modified so that at least 1 and preferably 2, 3, 4, 5, 6 or more of the transmembrane domains are eliminated. Preferably, the resulting modified protein forms a binding complex with at least one other protein and usually more than one other protein. As noted, the modified protein will inhibit normal function of the binding complex as assayed, e.g., by standard ligand binding assays or electrophysiological assays. Exemplary binding complexes are those which participate in electrical charge propagation such as those occurring in ion channel protein complexes. Typically, a dominant negative protein will exhibit at least 10 percent or greater inhibition of the activity of the binding complex; more preferably at least 20 percent or greater; and still more preferably at least about 30, 40, 50, 60, 70, 80, or 100 percent or greater inhibition of the binding complex activity relative to the full-length protein.

As a further illustration, a cDNA encoding a desired protein for use in the present methods can be modified so that at least one amino acid of the protein is deleted. The deleted amino acid(s) can be contiguous or non-contiguous deletions essentially up to about 1%, more preferably about 5%, and even more preferably about 10, 20, 30, 40, 50, 60, 70, 80, or 95% of the length of the full-length protein sequence.

Alternatively, the cDNA encoding the desired protein can be modified so that at least one amino acid in the encoded protein is substituted by a conservative or non-conservative amino acid. For example, a tyrosine amino acid substituted with a phenylalanine would be an example of a conservative amino acid substitution, whereas an arginine replaced with an alanine would represent a non-conservative amino acid substitution. The substituted amino acids can be contiguous or non-contiguous substitutions essentially up to about 1%, more preferably about 5%, and even more preferably about 10, 20, 30, 40, 50, 60, 70, 80, or 95% of the length of the full-length protein sequence.

Although generally less-preferred, the nucleic acid segment encoding the desired protein can be modified so that at least one amino acid is added to the encoded protein. Preferably, an amino acid addition does not change the ORF of the cds. Typically, about 1 to 50 amino acids will be added to the encoded protein, preferably about 1 to 25 amino acids, and more preferably about 2 to 10 amino acids. Particularly preferred addition sites are at the C- or N-terminus of the selected protein.

The present invention also provides a method of detecting an ion channel capable of serving as a drug target protein, the method comprising the following general steps 1) through 5):

1) providing a population of somatic cells capable of producing an ion current from a recombinant nucleic acid segment encoding an ion channel protein;

2) modifying the nucleic acid segment sufficient to alter the ion current produced by the encoded ion channel protein;
3) transferring the modified nucleic acid segment into the somatic cells under somatic cell gene transfer conditions which allow expression of the encoded ion channel and production of an altered ion current;
4) detecting the altered ion current; and
5) correlating the altered ion current to the capacity of the ion channel protein to serve as the drug target protein.

The expression of the ion channel protein can be increased or inhibited (e.g., by truncation) following the somatic gene transfer relative to a corresponding native gene. For example, the truncation can be a contiguous or non-contiguous deletion of the transferred gene. Alternatively, expression of the target protein can be inhibited by transfer of a gene encoding a modified protein comprising one or more amino acid substitutions relative to a corresponding native protein.

As noted, some of the target proteins of the method can form a binding complex with at least one other protein as in the case of certain ion channel proteins. For example, expression of the target protein in the method can be sufficient to produce a dominant negative protein that reduces or blocks function of the binding complex.

The present invention also features a method of reproducing human disease, e.g., diseases of electrically excitable cells such as cardiac cells and particularly a cardiac arrhythmia phenotype. In general, the method includes the following general steps 1) to 5):
1) providing a population of cultured somatic cells capable of producing an ion current from a recombinant nucleic acid segment encoding a selected ion channel protein;
2) modifying the nucleic acid segment sufficient to alter the ion current produced by the encoded ion channel protein;
3) transferring the modified nucleic acid segment into the cells under somatic cell gene transfer conditions which allow expression of the encoded ion channel and production of the altered ion current;
4) detecting the altered ion current; and
5) correlating the altered ion current to the capacity of the ion channel to serve as the therapeutic target. Typically, that correlation will include comparing the altered ion current to that ion current produced by the full-length protein (i.e. control assay).

The invention further provides a method of reproducing a cardiac arrhythmia phenotype in a population of cultured cells, the method comprising the following general steps 1) to 5):
1) providing a population of cultured somatic cells capable of producing an ion current from a recombinant nucleic acid segment encoding an ion channel protein;
2) modifying the nucleic acid segment sufficient to alter the ion current produced by the encoded ion channel protein;
3) transferring the modified nucleic acid segment into the cells under conditions which allow expression of the encoded ion channel and production of the altered ion current; and
4) detecting the altered ion current sufficient to reproduce the mammalian cardiac arrhythmia in the cultured cells.

Preferred methods include modifying the nucleic acid segments sufficient to overexpress the ion channel protein in the population of somatic cells. Further preferred are method in which the nucleic acids segments are modified to produce a dominant negative ion channel protein. The ion channel protein can be, e.g., a sodium, calcium, voltage-gated, or ligand-gated ion channel and particularly a potassium ion channel.

Disclosure relating to such channel proteins can be found in the discussion above and in U.S. Pat. No. 5,436,128 to Harpold, M. M et al.

Further provided by the present invention is a method of mimicking one or more effects of a drug candidate compound in an identified somatic cell, tissue or organ of interest, the method comprising the following general steps 1) and 2):
1) modulating, by somatic gene transfer, expression of a selected protein in selected cells; and
2) analyzing the result of expression of the protein to thereby predict the effect of the drug candidate compound.

Preferably the drug candidate compound would increase or suppress activity of the protein in the cell, tissue or organ. The method can further include use of a traditional drug discovery strategy such as those mentioned above and including natural products testing, synthetic chemical testing, etc., and use of the protein identified by the method.

As mentioned in the previous discussion, the present invention has significant uses.

For example, the methods are capable of identifying molecular targets of drug candidate compounds that would potentiate or suppress activity of those targets. The molecular targets include proteins which sometimes exist, e.g., as glycoproteins, lipoproteins, glycolipoproteins, or phosphorylated proteins. Alternatively, or in addition, the targets may be complexed to form a binding complex. Thus, the present invention can be used to identify molecular targets as they naturally occur inside selected cells, tissue or an organ.

The present invention can thus be used to select molecular targets suitable for testing, e.g., in traditional drug discovery methods such as those highlighted above.

Significantly, the present invention is complementary to traditional drug discovery methods and potentially enhances those methods by providing selected molecular targets, particularly in the absence of lead compounds.

Further contemplated uses of the present invention include assessment of the effects of existing drugs on selected somatic cells, tissues and organs that have been genetically modified to reproduce or mimic a human disease. The present invention can also be used as a research or medical tool to investigate the functional role of specified gene products in a desired cell, tissue, or organ. In addition, the present invention can be used to create animal models of human disease, e.g., by implanting the genetically modified cells into a suitable recipient in accord with the in vivo techniques mentioned above.

Additionally, the present methods can be combined with traditional drug discovery programs including the traditional screens outlined above to provide a comprehensive and rational drug screening program in which molecular targets are positively identified.

The present invention provides a number of significant advantages. For example, by identifying molecular targets of the drug candidate compounds, the methods can provide verification of a proposed or suspected molecular target. Alternatively, that verification can be advantageous toward the goal of understanding how an existing drug functions. As noted, such fundamental knowledge can be used as a starting point for implementation of a traditional drug discovery effort. Alternatively, that knowledge can also be used to focus an ongoing drug screen to identify those drug candidate compounds with likelihood of potentiating or suppressing an identified molecular target.

The present methods provide other significant advantages. For example, preferred assays of the invention employ living somatic cells, tissue or organs as screening media, thereby allowing molecular targets to be identified in a physiologically relevant setting.

Significantly, the present methods purposefully engage in the selection of molecular targets in the context of a desired cell, tissue or target tissue. In contrast, traditional drug screens often employ reconstituted or heterologous systems in well-studied model cells such as *Xenopus* or immortalized tissue culture cells. As noted, the present methods are not limited to these cells. Instead, the present methods can be used with nearly any cell, tissue or organ that is compatible with the somatic cell gene transfer techniques as discussed above.

The present methods provide even further advantages. For example, prior practice often required introduction of a cDNA encoding a modified protein of interest into the germ line of certain animals. The resulting transgenic animals usually have the nucleic acid segment incorporated into chromosomes (or deleted therefrom in the case of a "knockout" mutation).

In contrast, the present methods differ from conventional germ line transformation in that the methods use somatic gene transfer to achieve targeted expression of a desired protein. Thus, the present methods are compatible with de novo modification of isolated cells, tissues or organs. As noted above, the effects of a nucleic acid segment transferred in accord with the invention are fully manifested usually between several minutes up to one or two days or longer in culture. It is believed that in this setting, the result of expression of a modified protein more closely reproduces or mimics consequences of acute drug exposure. Approaches relying on germ line manipulations are believed to be particularly incompatible with that objective.

Significantly, the present methods are highly versatile and are compatible with analysis in variety of somatic cells, tissues, and organs. In particular, the present methods are relatively inexpensive to perform, and can be conducted in most laboratory settings.

Further advantages are provided by the present invention. For example, the methods support ongoing medical and research efforts that seek to understand known or suspected principles of drug action. As will become more apparent from the discussion and examples which follow, those principles can be readily testing by the present methods. Importantly, proteins modified and expressed in accord with the invention have highly specific functional alternations that reproduce or mimic potential drug actions in the selected somatic cell, tissue or organ.

Other aspects of the invention are discussed infra.

BRIEF DESCRIPTION OF THE DRAWINGS

FIGS. 1A–E are references to illustrative cDNA sequences that can be used in accordance with the present invention. Additional cDNA sequences are referenced in the text.

FIGS. 2A–F are graphs illustrating canine LV myocytes infected with AdGFP or AdHERG.

FIGS. 3B–C show the amino acid sequence of the Kv4.2Fl and Kv4.2ST proteins.

FIGS. 10A–B are graphs showing whole-currents of KV4.2ST.

FIGS. 12A–C are graphs showing that AdKv4.2St suppresses the A-type current of cerebellular granule neurons.

FIGS. 14A–I are graphs showing that modified Kv4.2ST (GFP-Kv4.2ST) specifically suppresses ShaI protein family currents.

DETAILED DESCRIPTION OF THE INVENTION

Figure 2B:
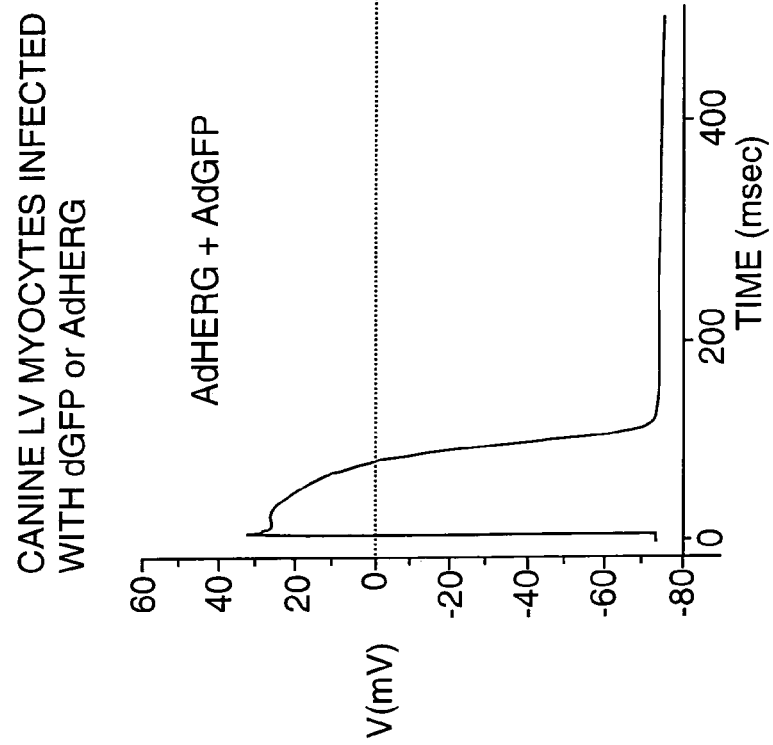

As discussed above, the present invention features methods and particularly in vitro assays for mimicking one or more effects of a drug candidate compound.

The ability to mimic the effects of a drug candidate compound and to identify the molecular target of that compound has been found to be very important. For example, it is believed that traditional drug screening approaches including those mentioned above may sometimes miss identification of promising drug candidates.

Particularly, several parameters related to performing traditional screens may negatively impact identification of the compounds, e.g., pleotropic effects, toxicity, or synergy manifested by the compound. In addition activity may be hidden by problems relating to solubility, permeability, stability or metabolism of the drug candidate compound in those screens.

In contrast, the present methods overcome many of these problems by predicting the effects of a drug candidate compound without complete knowledge of that compound and particularly without knowing the structure or synthesis of the compound.

In general, the present invention involves use of conventional techniques such as those relating to genetics, electrophysiology and recombinant DNA technology.

In particular, preparation of the nucleic acids disclosed herein involves standard recombinant manipulations, e.g., polymerase chain amplification reactions (PCR), preparation of plasmid DNA, cleavage of DNA with restriction enzymes, ligation of DNA, isolation of mRNA, introduction of the DNA into a suitable cell, culturing of the cell, SDS-PAGE gel electrophoresis, RNase protection assays, immunological techniques such as RIA, ELISA and Western Blot hybridization, Northern blots, scintillation coating, densitometry, construction of adenovirus vectors and autoradiography. See generally, Sambrook et al., *Molecular Cloning: A Laboratory Manual*. (2nd ed. (1989); Ausubel et al., *Current Protocols in Molecular Biology*, John Wiley & Sons, New York (1989), for discussion relating to many of the standard methods, the disclosures of which are incorporated herein by reference.

Further, methods for conducting electrophysiological experiments described herein include voltage-clamp type assays and measurement of whole currents. See e.g., Hille, B. supra; Miller C. (1987) *Neuromodulation: The Biological Control of Neuronal Excitability*. L. K. Kaczmark and I. B. Levitan (eds.) New York: Oxford University Press; and Armstrong, C. M. (1981) *Physiol. Rev.* 61: 644, the disclosures of which are incorporated by reference.

As noted, the present methods are in vitro assays that involve predicting the effect of a drug candidate compound, modulating, by somatic gene transfer, expression of a selected target protein in selected cells, and analyzing the result of expression of the target protein to predict the effect of the drug candidate compound.

As also noted, a nucleic acid segment suitable for use with the present methods is preferably a cDNA sequence encoding a full-length (or modified) protein. Typically, the cDNA will be formatted as a DNA vector appropriate for a somatic cell gene transfer technique as described herein. Preferred vectors are viral DNA vectors and particularly adenovirus vectors adapted for use with the techniques. Preferred adenovirus vectors and methods for performing somatic cell gene transfer have been described.

A cDNA suitable for use in accord with the invention can be obtained from a variety of public and commercial sources.

For example, one source is the National Center for Biotechnology Information (NCBI)-Genetic Sequence Data Bank (Genbank). A DNA sequence listing can be obtained from Genbank at the National Library of Medicine, 38A, 8N05, Rockville Pike, Bethesda, Md. 20894. Genbank is also available on the internet at. See generally Benson, D. A. et al. (1997) *Nucl. Acids. Res.* 25: 1 for a description of Genbank.

More particularly, Genbank provides a variety of cDNA sequences suitable for use with the present invention. Selection of a suitable cDNA from Genbank or another appropriate source of cDNAs will be guided, e.g., by the type of molecular target desired (i.e. enzyme, ion channel, etc.), the somatic cells, tissues or organ with which somatic cell gene transfer is to be performed, and the mode of viral gene delivery selected.

FIG. 1 below provides an illustrative list of cDNA sequences obtained from the Genbank database that can be used with the present methods. The figure lists proteins encoded by the cDNA sequences under "Description" and cites reference designations under "Reference" and "mRNA/gene sequence" in accord with nomenclature adopted by Genbank. The cDNA sequences can be readily accessed on-line by using the designations provided by Genbank.

For example, referring again to FIG. 1, a suitable cDNA sequence is the potassium channel beta 1a subunit. That cDNA can be accessed on-line by referencing the designation U33428. In addition, other reference designations are provided in the figure for that channel subunit.

See also the examples which follow for an illustrative use of the KvS4.2FL potassium channel cDNA sequence.

It is possible to obtain cDNA sequences from Genbank by one or a combination of alternative approaches.

For example, one approach is to perform a routine PCR experiment based on the provided cDNA sequence information.

In a specific approach, a complimentary pair of opposing oligonucleotide primers can be made that are spaced between about 100 to 5000 kb apart, preferably about 200, 300, 400, 500, 700, 800, 900 to 4000 kb apart, and more preferably about 1000 kb apart depending, e.g. on the size of the selected cDNA. The cDNA can be amplified and purified according to standard methods. The amplified DNA is then inserted into a somatic cell gene transfer vector such as preferred adenovirus vectors described below for somatic cell gene transfer. Typically, the cDNA will be ligated to a suitable oligonucleotide linker (i.e. a polylinker) at each end of the cDNA so that the nucleic acid can be ligated to the vector with one or more known restriction sites. See the examples which follow.

As mentioned previously, the present invention can be used with a nucleic acid segment and particularly a cDNA that encodes a protein of known or unknown function.

For example, if the cDNA encodes a protein of unknown function, it is possible to determine phenotypic consequences of overexpressing or making a dominant negative of that protein by strategies known in the field.

For example, one such strategy is to assign a function to that unknown protein. That can be achieved by determining homology between the unknown protein and one or more other proteins of known function. That assignment is usually based on amino acid sequence homology to another protein of known or suspected function.

It is generally recognized that a significant majority of unknown proteins can be assigned a function by that strategy.

Two or more proteins are "homologous" to each other if the amino acid sequence of each protein shares at least 25%, more preferably at least 40%, and even more preferably at least 50% or more amino acid sequence identity over at least 100 amino acids after performing what is known in the field as amino acid gapping. A variety of standard computer-assisted programs are available for conducting protein homology determinations and function assignments such as those specifically referenced below.

In particular, the following well-known computer algorithms can be used to assign function to an unknown protein: FASTA, TFASTA and BLAST. Those computer alogorithms and instructions for use thereof are available at the NCBI. Additional useful computer programs generally available in the field include the Chou-Fasman algorithm and the algorithm reported by Kyte and Doolittle. See e.g, Kyte, J. and R. F. Doolittle (1982) *J. Mol. Biol.* 157: 105; Chou, P. Y and G. D. Fasman (1974) *Biochemistry* 13: 222.

In many instances, it will be useful to conceptually translate a cDNA of interest and particularly a cDNA encoding an unknown protein, with the TFASTA, FASTA or BLAST algorithms. As is well-known, these algorithms can identify a variety of motifs in the encoded protein, particularly transmembrane, extracellular and intracellular domains, signal sequences and poly-adenylation sequences. The alogrthms often include standard hydropathy plot analysis to identify the transmembrane domain and other domains of interest.

Thus, in instances where is it desirable to make a dominant negative of a membrane protein and particularly an ion channel protein, it will be useful to map the transmembrane domains. That map will facilitate deletion of selected transmembrane domains to create a desired dominant negative mutation.

Alternatively, the transmembrane domains of many membrane proteins and particularly ion channel proteins are known and can be deleted in accordance with the discussion above and the examples which follow to make a desired dominant negative protein.

A cDNA of interest that has been modified to encode a dominant negative protein can be a dominant negative membrane protein such as an ion channel protein. That encoded protein can be readily tested by a variety of recognized electrophysiological methods including standard analysis in *Xenopus* oocytes. In general, those oocytes are not usually electrically responsive but they can be made so by introduction of specified ion channel proteins in accord with standard methods. Preferred cDNA constructs encode a dominant negative ion channel in which at least one transmembrane domain has been deleted up to the penultimate number of transmembrane domains in the corresponding native protein. See e.g., Hille, supra and the examples which follow for conducting assays to detect dominant negative ion channel mutations and in particular, patch-clamp type and whole current assays to accomplish same.

Dominant negative approaches have been used to map levels of specific ion channel proteins in neurons from *Xenopus*. See Ribera, A. B. (1996) *J. of Neuroscience* 16: 1123.

More specifically, in the examples below, a strategy is outlined a strategy for making and testing a dominant negative mutation of the KsV4.2 potassium channel.

As noted above, a nucleic acid segment and particularly a cDNA can encode a protein of known function. A variety of recognized tests are available for assaying the function (or functions) of known proteins. Exemplary of such tests include, but are not limited to, recognized tests that can detect cell proliferation, growth, or differentiation; tests for detecting replication, transcription, translation, protein processing including degradation, tests for cell death including apoptosis and necrosis, cell viability tests; cell adhesion tests; kinesis and particularly pathfinding tests; neovascularization tests, oncogenic transformation tests; tests to detect small molecules such as cytokines, cyclic nucleotides, or hormones; enzyme tests; and receptor-ligand binding tests.

Additional recognized tests are as follows. As noted above, the tests are usually conducted following somatic cell gene transfer and expression of the protein of interest.

For example, one recognized test is a standard cell proliferation assay.

In particular, a selected cDNA can modified as described above to encode a modified protein of interest. For example the encoded protein could be an enzyme which can modulate, e.g., inhibit, cell proliferation by at least 25%, preferably at least 50%, or more relative to a suitable control assay. Exemplary cell proliferation assays include counting viable cells and monitoring activity of specified citric acid cycle enzymes such as lactate dehydrogenase. A preferred assay measures incorporation of one or more detectably-labelled nucleosides into DNA, e.g., by:

a) culturing cells transformed by somatic cell gene transfer in medium and adding) a radiolabelled nucleoside such as $^3$H— thymidine in an amount between about 0.1 to 100 μCi;

b) incubating the cells for about 6–48 hours followed by washing; and c) measuring incorporation of the 3H— thymidine into DNA over that time relative to a control culture that is prepared and incubated under the same conditions as the assay culture but does not include the potential GalT-2 modulating compound. The measurement can be achieved by several methods including trichloroacetic acid (TCA) precipitation of labeled DNA on filters followed by scintillation counting. See e.g., Chatterjee, S., *Biochem. Biophys. Res Comm*. (1991) 181:554 and references cited therein for disclosure relating to this assay.

Additional examples of recognized cell proliferation assays employ cells of the circulation system, e.g., smooth muscle cells and particularly myocytes prepared according to standard methods. See e.g., Ross, R. *J. Cell. Biol.* (1971) 50:172; Chatterjee, S. et al. (1982) *Eur. J. Biochem.* 120: 435; Bergmeyer, H. V. *In Principles of Enzymatic Analysis.* (1978) Verlag Chemie, NY; and Hilal-Dandan, R., and Khairallah, P. A. (1991) *J Mol Cell Cardiol* 23, 705.

Another suitable assay is a cell adhesion assay. In this case, a cDNA is chosen and modified as described. The modified protein, e.g., a membrane protein, preferably modulates, e.g., inhibits, cell adhesion by at least 25%, preferably at least 50%, or more relative to a suitable control assay For example, a preferred cell adhesion assay is achieved by:

a) labeling a first population of cells, particularly immune cells such as certain leukocytes, with a detectable label which can be a chromatic, radioactive, luminescent (e.g., fluorescent, or phosphorescent), or enzymatic label capable of producing a detectable label;

b) contacting the first population of cells with a second population of cells such as certain endothelial cells associated with vascular intima, which cells have been detectably-labelled with a chromatic, radioactive, luminescent (e.g., fluorescent, phosphorescent), or enzymatic label preferably different from the label employed in step a); and c) detecting any adhesion between the first and second population of cells. The detection can be achieved by a variety of methods such as microscopy, particularly fluorescence-based photomicroscopy involving FACS; automated cell sorting techniques, immunological methods such as ELISA, RIA; and scintillation counting.

Additional assays include standard oncogenic transformation assays that include monitoring growth in liquid or semi-solid media. The assay is based on recognition that most eukaryotic cells exhibit a phenomenon known as contact inhibition. However, transformed cells lose that contact inhibition and can grow in liquid or semi-solid growth media in a transformed (malignant) state. Preferably, the modified protein encoded by the nucleic acid segment modulates, e.g., inhibits, oncogenic transformation by at least 25%, preferably at least 50%, or more relative to a suitable control assay.

In addition, a variety of molecular assays can be employed to determine phenotypic consequences of expressing a modified protein in accordance with the invention.

For example, Northern blot assays can be performed to quantitate expression of a particular modified protein relative to a suitable control assay. Oligonucleotide primers can be readily made from the cDNA sequences and used as probes to perform the Northern blots. Generally, the oligonucleotide primers will be between 12 and 50 nucleotides in length, preferably between about 15 and 20 or 25 nucleotides in length. Alternatively, the oligonucleotide primers can be used to perform Polymerase Chain Reaction (PCR) amplification of a desired cDNA sequence (using, e.g., genomic template DNA or preferably a commercially available cDNA library known to include the cDNA) and that amplified cDNA can be used to perform the Northern blot assay. Preferred Northern blot assays involve quantitating mRNA and correlating the amount of mRNA expressed in cells, tissues or organs with the amount of mRNA produced by a full-length cDNA sequence (control). Particularly preferred assays include testing for RNase protection such as described in the examples below.

Further, a variety of immunological methods can be employed to determine the phenotypic consequence of expressing the modified protein. For example, the modified can be quantitated by a standard immunological methods, e.g., ELISA, Western blot, or RIA. Suitable antibodies and particularly monoclonal antibodies for use in the methods can be obtained from Linscott's Directory (40 Glen Drive, Mill Valley Calif. 94941), and by the American Type Culture Collection (ATCC) 12301 Parklawn Drive, Rockville, Md. 20852.

Additional specified tests can be found in the references cited in FIG. 1. Those references disclose tests for assaying a variety of proteins including certain ion channel proteins including specified calcium, sodium, potassium, voltage-gated, and ligand gated channels, certain growth factors and enzymes, particular onocogens and proto-oncogenes, and cell death proteins.

See also Hille, B., supra, Kaczmark and Levitan, supra; and Armstrong, C. M. supra for general disclosure relating to tests for to ion channel proteins. See further the examples which follow for specific electrophysiological tests relating to a potassium channel protein.

As noted, preferred tests include electrophysiological assays in which a cDNA encoding a modified protein is introduced into selected cells, tissues or an organ by somatic cell gene transfer. Typically, the cells are electrically responsive, but as mentioned above the cells may include certain oocytes that are not usually responsive to charge. Following transfer of the cDNA into the cells, tissue or organ, whole-currents are measured with a voltage clamp implementation. Preferably, the assay is performed about 24 hours to 72 hours, preferably 30 to 60 hours and more preferably 42 to 50 hours after introduction of the transgene. Preferred cells include cerebellular granule neurons and adult cardiac myocytes. See the examples which follow.

All documents mentioned herein are incorporated herein by reference.

The invention is further illustrated by the following non-limiting examples.

EXAMPLE 1

Production of Constructs Overexpressing an HERG Potassium Current Gene

The HERG gene encodes a potassium current known as $I_k$. The HERG gene was overexpressed in canine ventricular myocytes using viral gene transfer manipulations described above.

EXAMPLE 2

Result of Overexpressing an HERG Potassium Current Gene

The vector constructs prepared in Example 1 were introduced into canine ventricular myocytes by somatic cell gene transfer. After 24 to 72 hours, transduced myocytes were tested by patch-clamp electrophysiology in accord with methods described above and in SoKaab et al. (1996) *Circulation Res.* 78: 262.

Figure 2A:
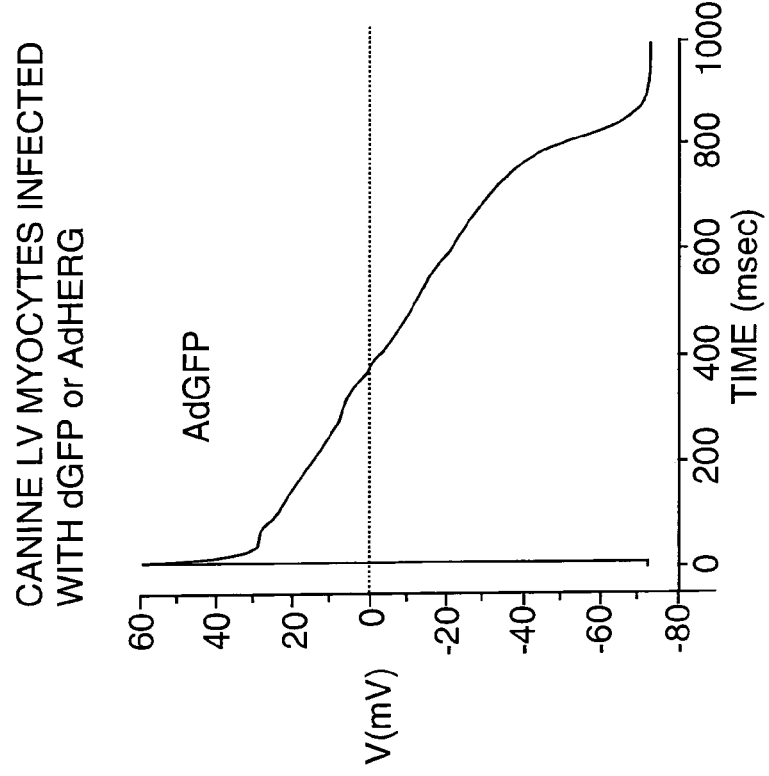
Figure 2F:
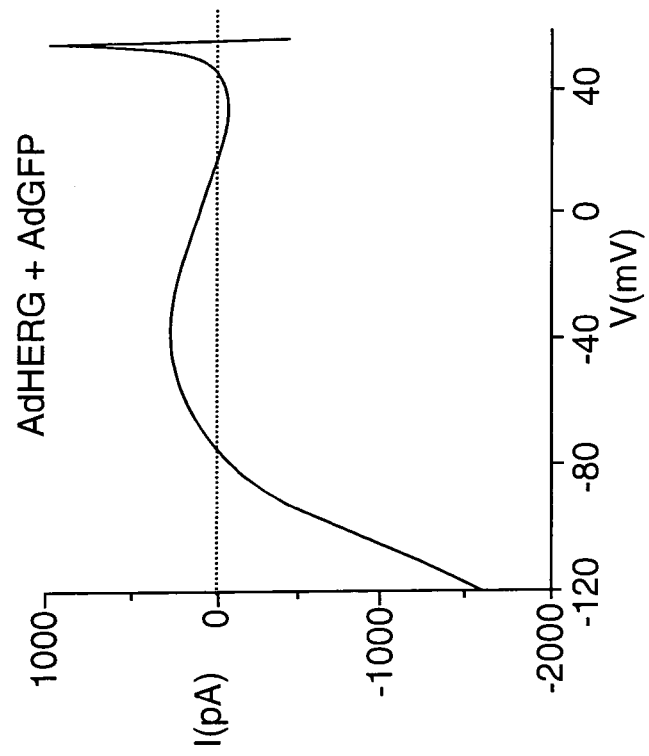
Figure 2E:
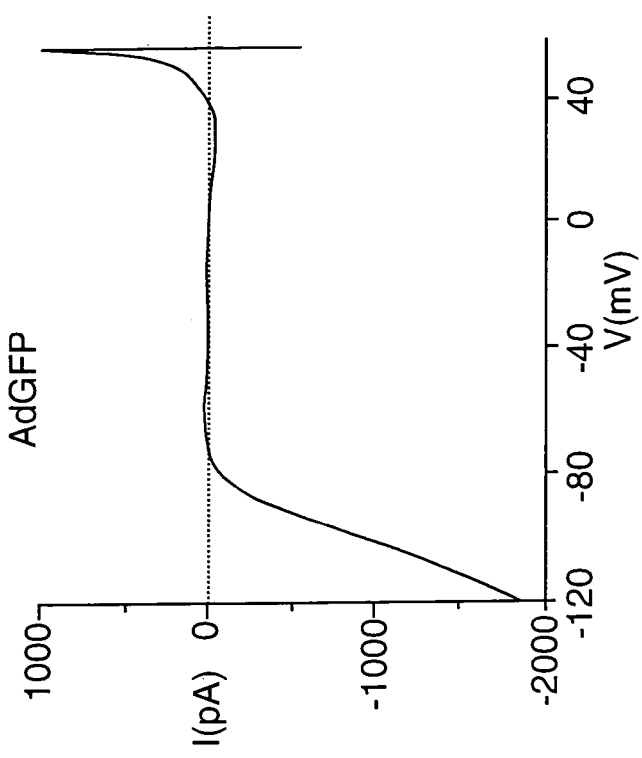

FIGS. 2A–F compare the electrical properties of a cell infected with a reporter gene (GFP) as a control (FIGS. 2D–F) to those of a cell overexpressing HERG (FIGS. 2A–C). Action potentials are abbreviated in the HERG-infected cell (top panels); this would be a useful therapeutic effect in patients with ventricular arrhythmias related to abnormal repolarization. The lower panels confirm that $I_k$ has been functionally overexpressed. Thus, this cell reproduces the phenotype that would result from exposure to a selective pharmacologic agonist of HERG. Other functional tests such as numerical simulation and/or quantitation time modulation or cell or organ function could be applied to such cells, or to tissues similarly modified, in order to verify or to disprove the therapeutic utility of the agonist effect.

EXAMPLE 3

Production of Constructs Expressing a Dominant Negative Kv4.2 Voltage-Dependent Potassium Channel Gene Potassium channel gene products have been reported to form functional channels when four identical (or closely related) subunits come together as a tetramer; all four subunits must be functional in order for the channel complex to be functional. We have found that by deleting one or more transmembrane domains of the potassium channel, it is possible to create dominant negative mutant potassium channel proteins that block normal function of the channel complex.

There is no known pharmacological inhibitor for the transient outward current ($I_{10}$) formed by some potassium channel genes. Kv4.2 is an example of a voltage-dependent potassium channel gene that is expressed in mammalian heart muscle and which is believed to encode $I_{10}$.

There follows a description of a truncated version of Kv4.2 (Kv4.2ST). This construct was designed to multimerize with and cripple full-length products of the Kv4 gene family. The truncated construct described here includes the first transmembrane segment (S1). Thus, it was believed that Kv4.2ST would contain determinants of multimerization but would otherwise be non-functional. Such a protein would function as a dominant negative protein.

Figure 3A:
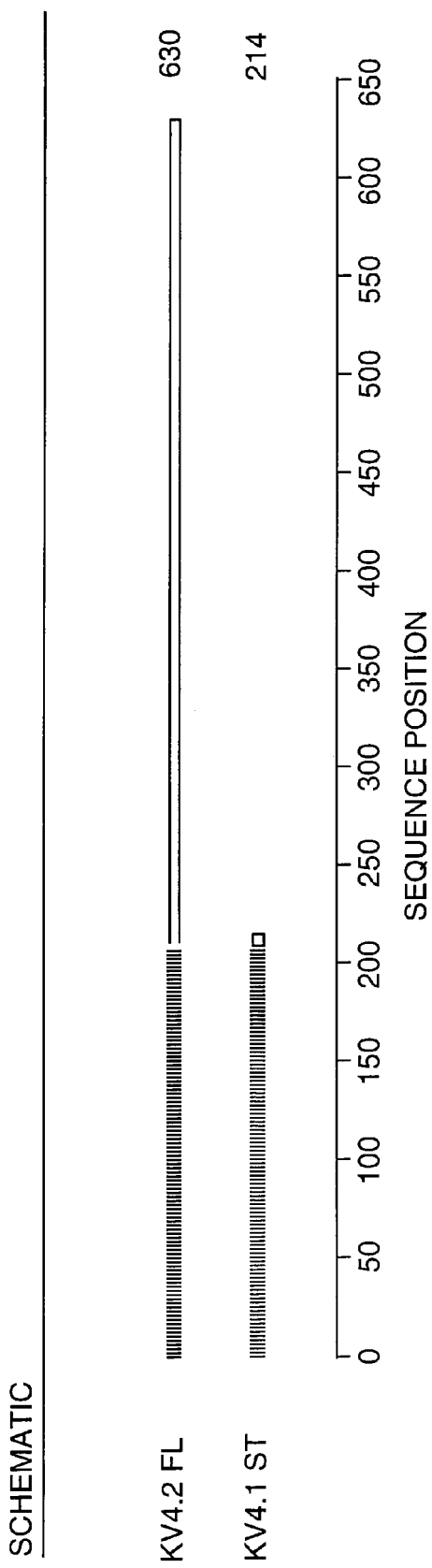
FIG. 3A is a graphical illustration of the KV4.2FL and KV4.2ST ion channel proteins.

Kv4.2 and related family members were "knocked-out" by creating Kv4.2 ST. FIGS. 3A–C summarizes the strategy used by presenting the Kv4.2 (SEQ ID No. 1) and Kv4.2ST (SEQ ID NO. 2) amino acid sequences and comparing those sequences by length. More specifically, FIGS. 3A–C compare full-length Kv4.2 (Kv4.2FL) and truncated Kv4.2ST proteins using a bar motif FIGS. 3B–C (SEQ ID Nos. 1,2) provide the amino acid sequences of the Kv4.2FL and Kv.2ST proteins.

Figure 4B:
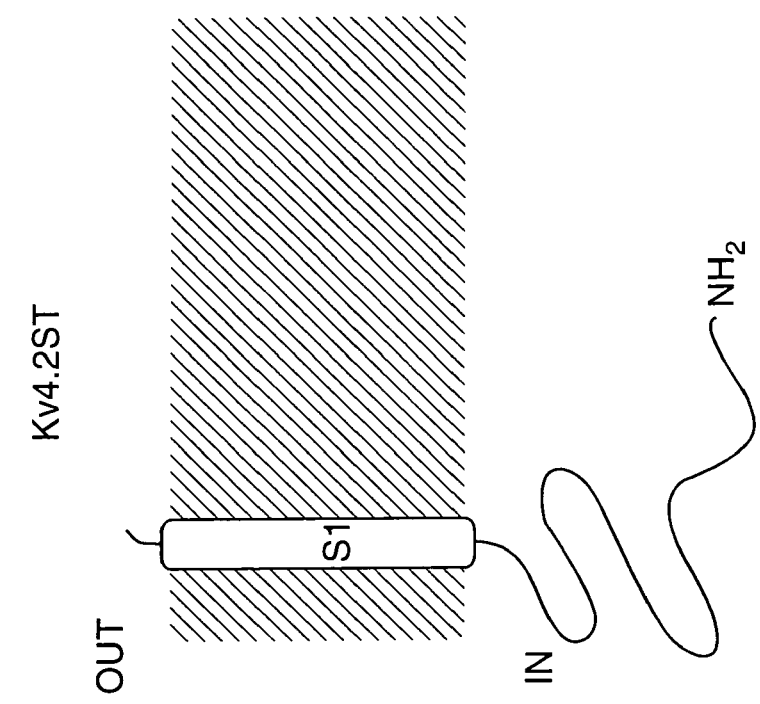
FIGS. 4A–B are schematic representations of the Kv4.2 (4A) and Kv4.2ST (4B) proteins.
Figure 4A:
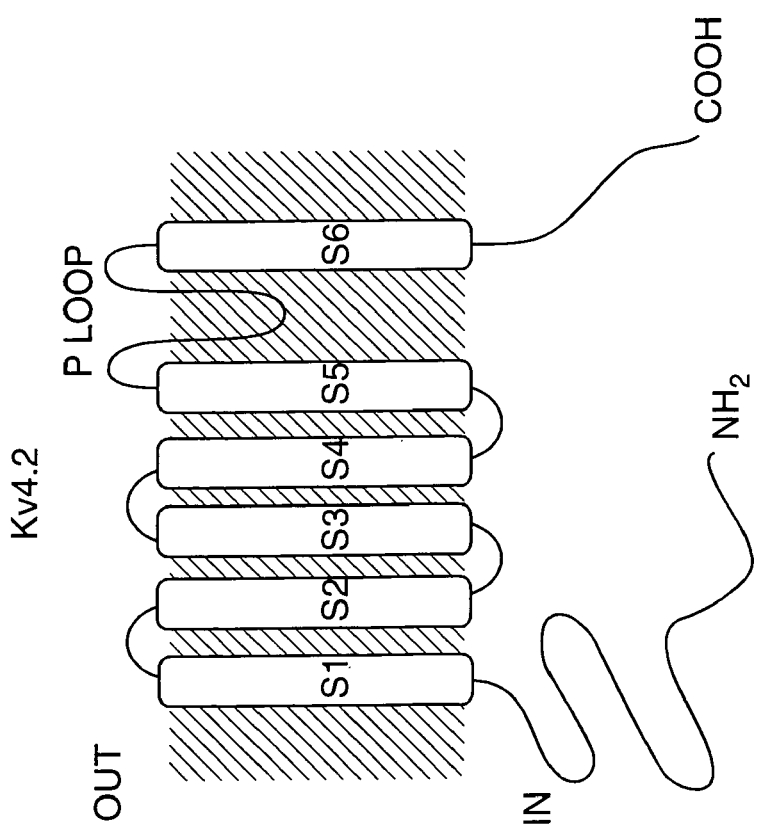

FIGS. 4A–B provide a schematic illustration of the full-length Kv4.2 (FIG. 4A) and Kv4.ST proteins (FIG. 4B) in a cell membrane. More particularly, FIG. 4A is a topology diagram depicting the structure of the full length Kv4.2 channel (FIG. 4A) next to the predicted structure of the Kv4.2ST protein (FIG. 4B).

The coding sequence for the rat Kv4.2 potassium channel gene was provided by M. Tamkun (Vanderbilt University). The portion of the sequence coding for the first 206 amino acids (FIG. 4A) was amplified by PCR using primers which contained unique restriction sites on the 5' and 3' ends. The product (Kv4.2ST) was cloned into pSL301 (Invitrogen, San Diego, Calif.) and sequenced to confirm the absence of PCR-induced mutations. The Kv4.2 ST sequence was then cloned into the adenovirus shuttle vector pE1CMV (FIG.

Figure 5:
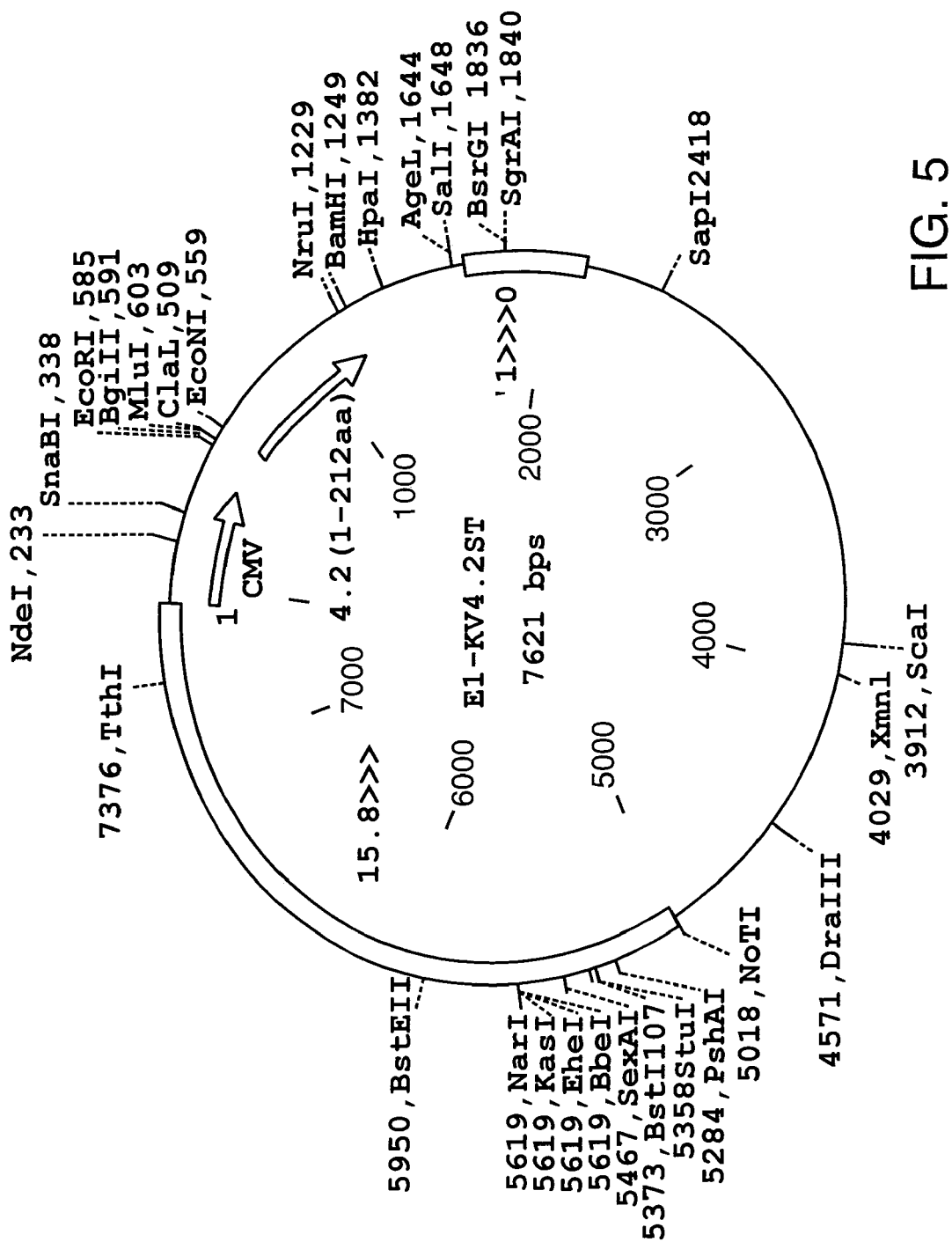
FIG. 5 is a map of the E1-KV4.2ST vector.

4B). Constructs were made in both the sense and antisense orientations with respect to the promoter, designated pE1Kv4.2ST and pE1CKv4.2AS respectively. An additional vector, pE1RKv4.2AS, contains the Rous sarcoma virus (RSV) long terminal repeat (LTR) as the promoter and was used to generate AdRKv4.2AS. The pE1Kv4.2ST vector is shown in FIG. 5. See Morgan, R. A., et al. (1992) *Nucle. Acids Res.* 20:1293; Johns, D. C., et al. (1995) *J. Clin. Invest.* 96:1152.

The 4.2ST sequence was also fused in frame to the enhanced green fluorescent protein (EGFP) sequence in the vector pEGFP-C3 (Clontech, Palo Alto, Calif.) to make the construct pEGFP-4.2ST. The full-length Kv4.2 sequence was subcloned into pREP4 (Invitrogen, Carlsbad, Calif.) and into the pEGFP-C3 backbone to make pRep4.2FL and pE-Kv4.2FL respectively. The full-length rat Kv4.3 sequence was obtained from B. Rudy (New York University Medical Center) and cloned into the expression vector pGFPIRS. This vector is a modified version of pEGFP-C3 which contains the polio virus internal ribosomal entry site (IRES), obtained from G. Ketner (Johns Hopkins School of Public Health) cloned between the EGFP sequence on the 5' side and the polycloning site on the 3' site. This vector (pGFPIrKv4.3) produces a single transcript encoding both the EGFP protein and the Kv4.3 protein. See Morgan, R. A., et al. (1992) *Nucl. Acids Res.* 20:1293;

The human inward rectifier cDNA (Kir2.1) containing the inactivating mutation of GYG to AAA, (Tinker, A., et al. (1996) *Cell* 87:857) was provided by G. Tomaselli (Johns Hopkins University) and was fused to the EGFP sequence in pEGFP-C3 (pGFPKir2.1-AAA). The CMV-β galactosidase plasmid contains the *E. coli* lacZ gene under the control of the CMV immediate early promoter. The mitochondrial targeted GFP (mtGFP) sequence was provided by M. Rizzuto (University of Padova). The mtGFP sequence was similarly subcloned into the shuttle vector pE1CMV to make pE1CMVmtGFP. The humanized GFP was subcloned from the vector pGreenLantern (Life Technologies, Gaithersburg, Md.) into pE1 CMV to create pE1CMVhGFP. Mammalian expression vectors containing full-length Kv1.4 and Kv1.5 sequences were supplied by E. Levitan (University of Pittsburgh) and L. Philipson (University of Chicago), respectively. See Rizzuto, R., et al. (1995) *Curr. Biol.* 5:635; Philipson, L. H., et al. (1993) *Biochem. Biophys. Acta.* 1153:111.

EXAMPLE 4

Production of Gene Transfer Constructs

Figure 6:
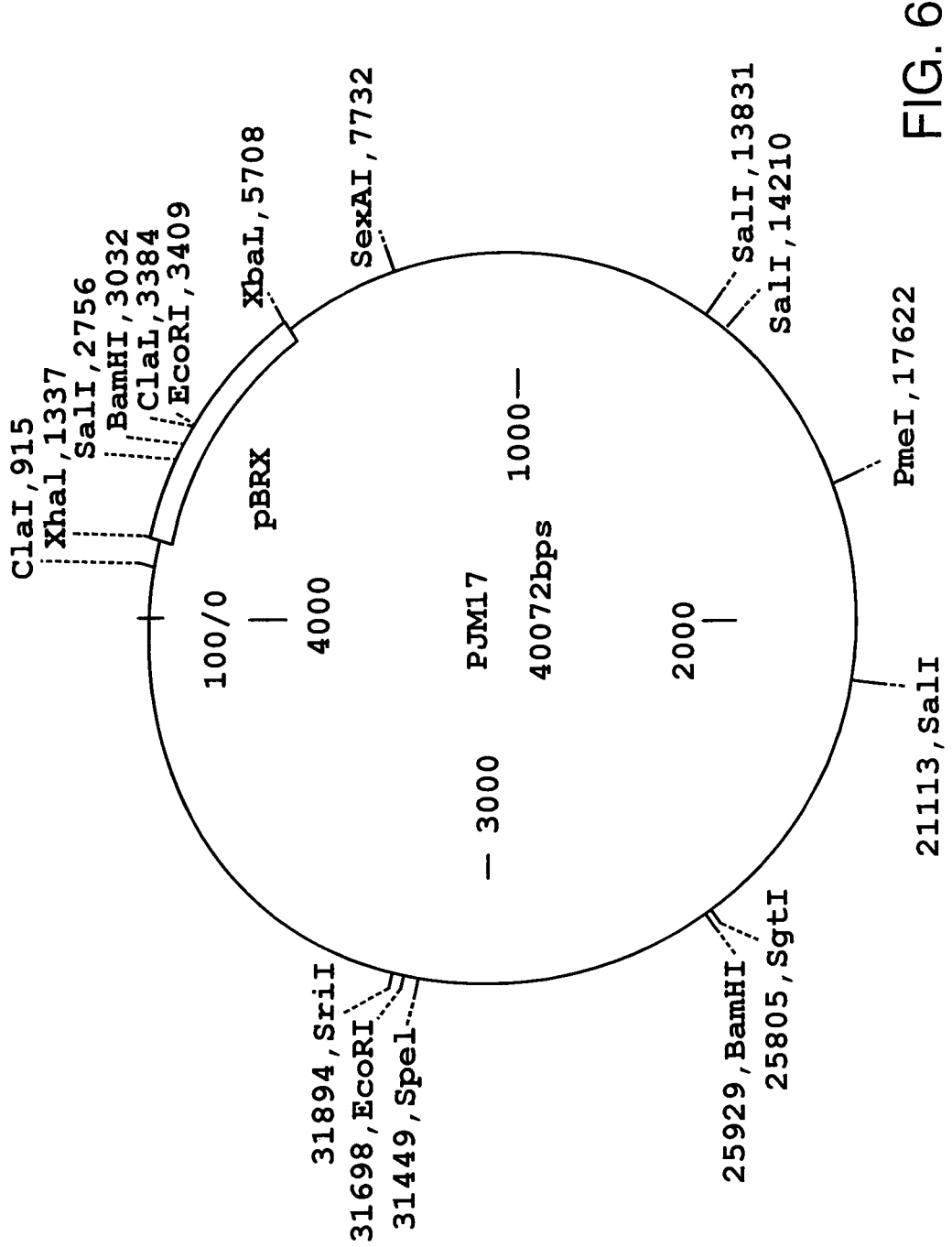
FIG. 6 is a map of the pJM17 vector.

The strategy is outlined in FIG. 4B. The various adenovirus shuttle plasmids were cotransfected with pJM17, containing the full human adenovirus serotype 5 genome, (McGrory, W. J., et al. (1988) *Virology* 163:614) into HEK293 cells using Lipofectamine (Life Technologies Inc., Gaithersburg, Md.). As previously described, homologous recombination between the shuttle vector and pJM17 replaces the region of the adenovirus between map units 1.0 and 9.8 with the expression cassette containing the desired cDNA. Successful recombinations were screened either by direct visualization (AdmtGFP and AdhGFP) or by Southern blot analysis of small scale infections (Ad4.2ST and AdC4.2AS and AdR4.2AS) followed by RNase protection assays of RNA made from infected cells as described below. AdCMVβ-Gal contains the β-gal gene driven by the CMV promoter and was provided by G. Wilkinson (University of Wales College of Medicine, Cardiff, U.K.). The pJM17 vector is illustrated in FIG. 6.

Using standard cloning methods, the Kv4.2 ST was inserted into adenovirus to form a replication-deficient recombinant gene transfer construct, AdKv4.2ST. The recombination strategy is outlined in FIGS. 7A and 7B.

Figure 7A:
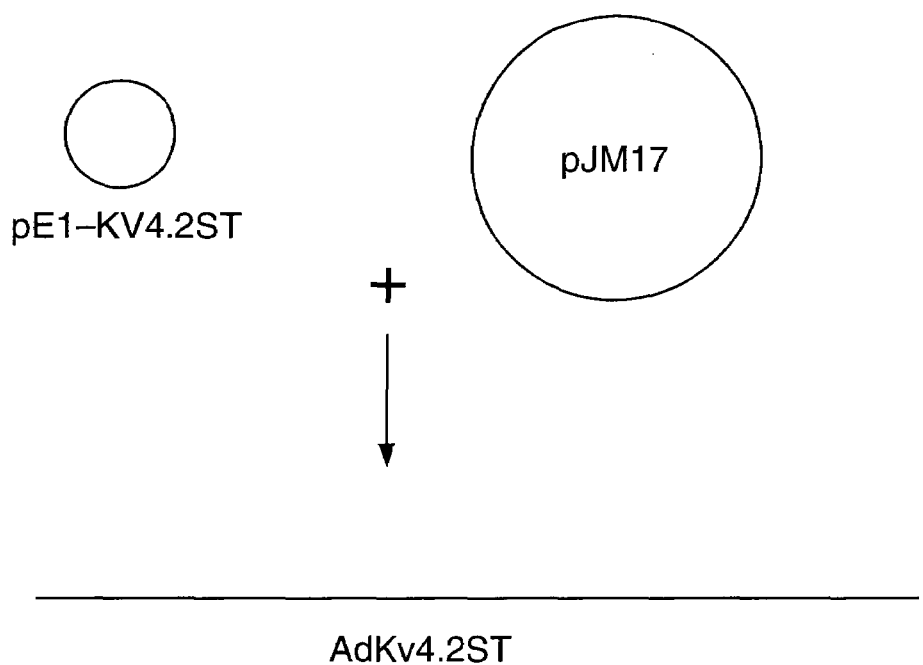
FIG. 7A outlines a recombination strategy for making the KV4.2ST vector.
Figure 7B:
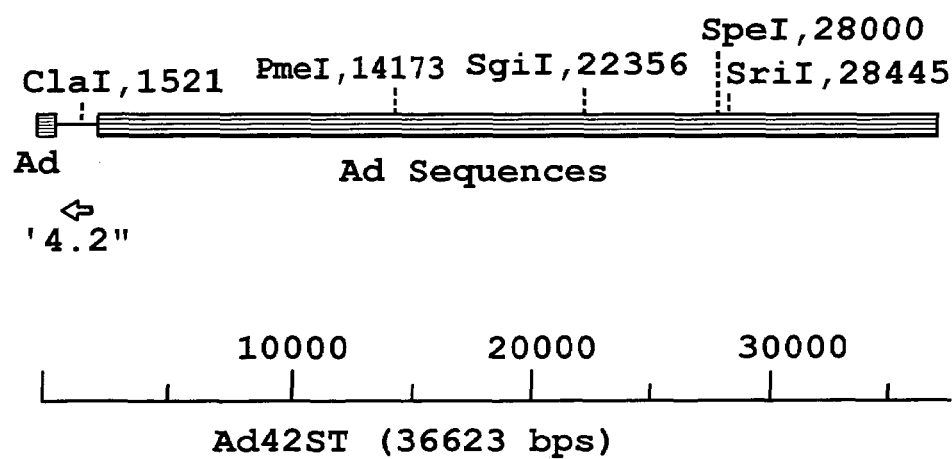
FIG. 7B depicts the map of the Ad4.2ST sequence resulting from the strategy outlined in FIG. 7A.

FIGS. 7A and 7B are further explained as follows. Cotransfection of the adenoviral shuttle vector pE1Kv4.2St and the bacterial plasmid pJM17 in HEK293 cells results in a recombinant adenovirus. This recombination replaces the E1 region of the adenovirus with Kv4.2ST expression cassette.

The somatic cell gene transfer protocol enables efficient infection of a variety of tissues, including the heart.

EXAMPLE 5

Molecular Analysis of Expressed Potassium Channel Genes

Viral DNA was isolated as previously described (Hitt, M., et al. (1994) *Cell Biology: A Laboratory Handbook* pp. 479). DNA was size separated by agarose gel electrophoresis and blotted onto Nytran nylon membranes using a Turboblotter apparatus (Schleicher and Schuell, Keene, N. H.). Blots were pre-hybridized and hybridized in Rapid-hyb buffer (Amersham Life Sciences, Arlington Heights, Ill.). Probes were labeled using a random primed labeling kit (Boehringer-Mannheim, Indianapolis, Ind.) and ($\alpha$-P$^{32}$) dCTP (New England Nuclear, Boston, Mass.).

Total RNA was isolated from HEK293 cells using Trizol reagent (Life Technologies, Gaithersburg, Md.). Ribonuclease protection assays were performed using the RPAII kit (Ambion, Austin, Tex.). Ten micrograms of total RNA was hybridized to both sense and antisense RNA probes for the Kv4.2ST sequence. Protected fragments were separated on a 5% denaturing polyacrylamide gel.

Southern blot analysis of isolated viral DNA confirmed the presence of the Kv4.2ST sequence in the recombinant adenovirus. RNase protection analysis of total RNA isolated from HEK293 cells which had been infected with either AdKv4.2ST, AdCKv4.2AS or AdRKv4.2AS revealed that only sense and antisense (respectively) RNAs were expressed from these constructs in detectable amounts (see FIG. 8).

Figure 8:
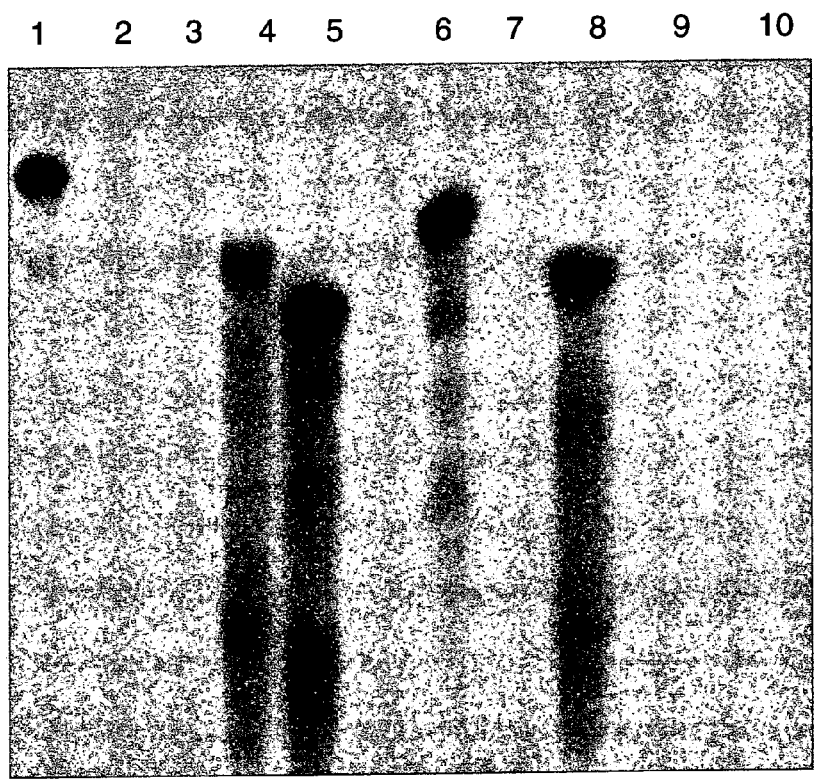
FIG. 8 is a representation of an RNase protection assay blot showing that AdKv4.2ST expresses only the sense strand of the Kv4.2ST sequence.

FIG. 8 is explained as follows. RNase protection assay using both sense and anti-sense probes (Lanes 1,6) hybridized to yeast RNA (lanes 2 and 7), total RNA from HEK293 cells infected with AdKv4.2ST (lanes 3 and 8), or total RNA from cells infected with AdRKv4.2AS or AdCKv4.2AS (lanes 4&9 and 5&10 respectively). FIG. 8 shows that AdKv4.2ST expresses only the sense strand of the Kv4.2ST sequence.

EXAMPLE 6

Transfection of Kv4.2 Potassium Current Genes into CHO-K1 Cells

CHO-K1 cells (CCL-61 American Type Culture Collection, Rockville, Md.) were grown in Ham's F-12 media (CellGro, Mediatech, Washington D.C.) supplemented with 10% fetal bovine serum (LifeTechnologies, Gaithersburg, Md.) at 37 C.° in a 5% $CO_2$, humidified incubator. Cells were split and plated at 30–40% confluency on coverslips in six well plates 24 hours before transfection. Cells were transfected with plasmid DNA (1 μg/well total) using Lipofectamine (LifeTechnologies, Gaithersburg, Md.). After a four-hour exposure cells were washed once with normal growth media and then incubated for one to two days in normal growth media under normal growth conditions.

Figures 9A, 9B, 9C:
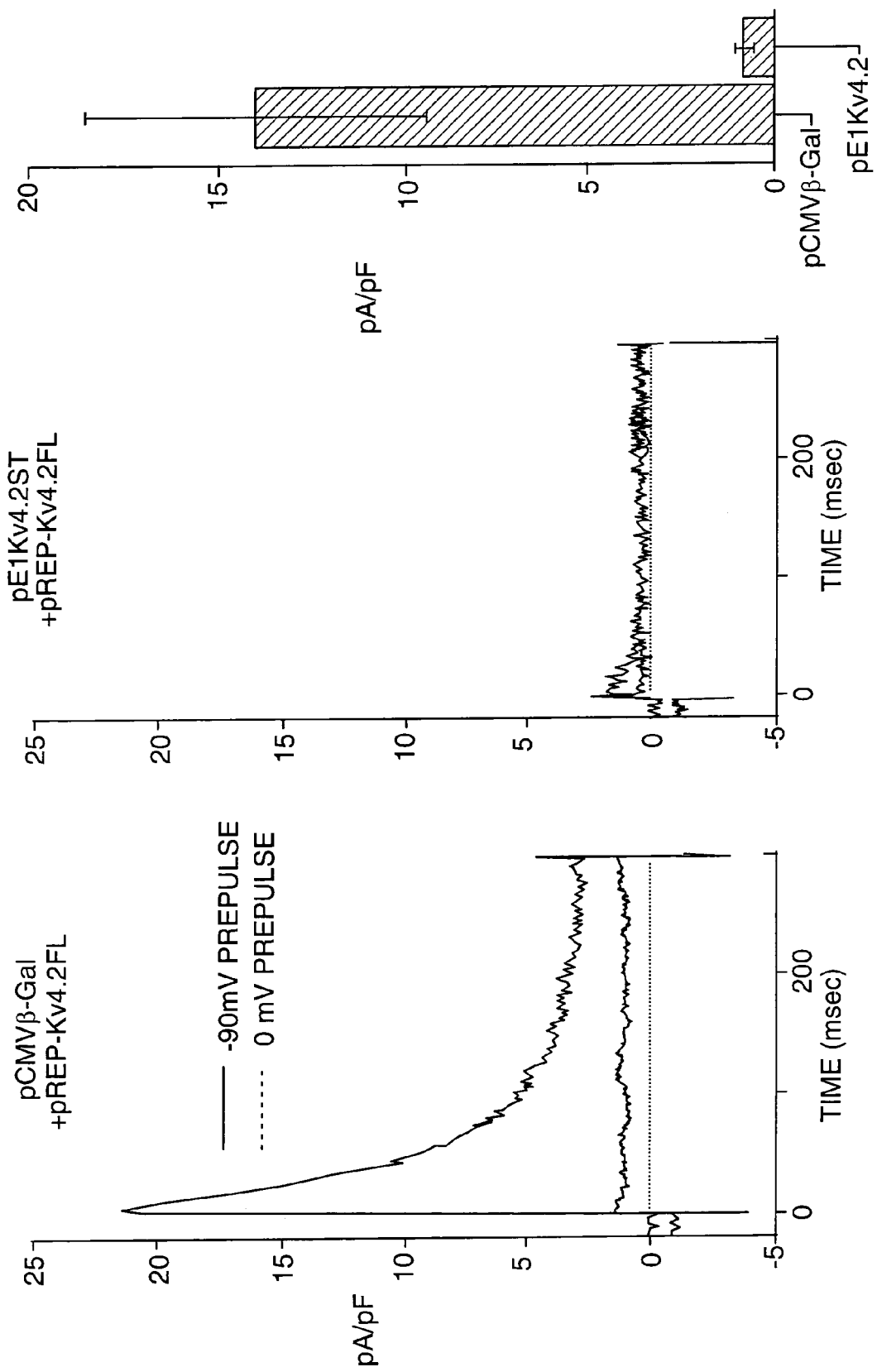
FIGS. 9A–F are graphs showing specific suppression of Kv4.2 currents by pE1Kv4.2ST.
Figure 9F:
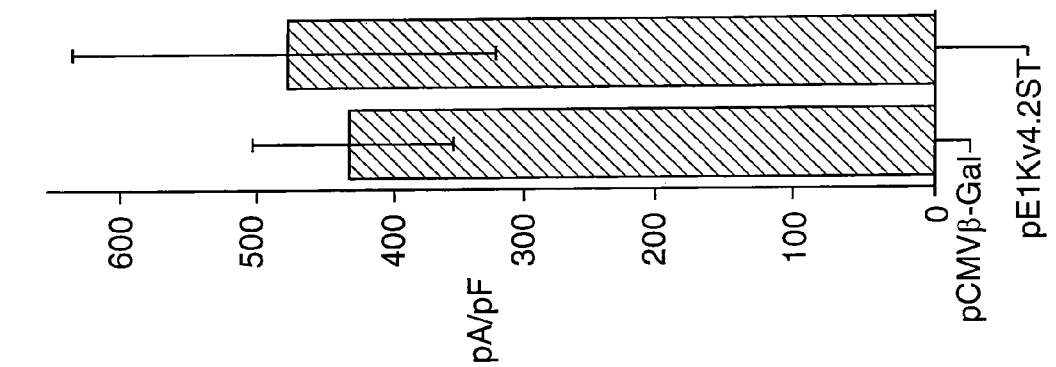

When cotransfected into CHO-K1 cells, Kv4.2ST suppresses functional expression of a full-length Kv4.2 construct (FIGS. 9A,B,C). These experiments were done at a 2:1 molar ratio of pE1Kv4.2ST: pRepKv4.2FL based on preliminary experiments in which the currents were found to be much more variable at molar ratios of 1:1 and 1:2. Suppression of Kv4 current is specific, as cotransfection of Kv4.2ST with a Kv1.5 expression vector (also at a 2:1 molar ratio) does not affect functional expression of this channel (FIGS. 9D,E, F). These results encouraged the production of the recombinant adenovirus containing this construct (AdKv4.2ST), for infection of neurons and cardiac myocytes which are notoriously difficult to transfect by conventional means.

Figure 9E:
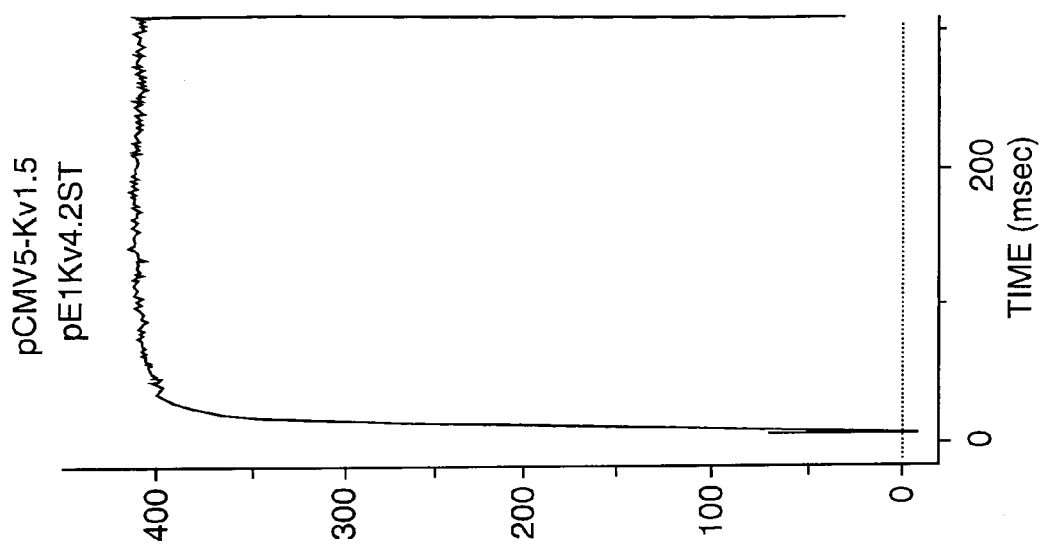
Figure 9D:
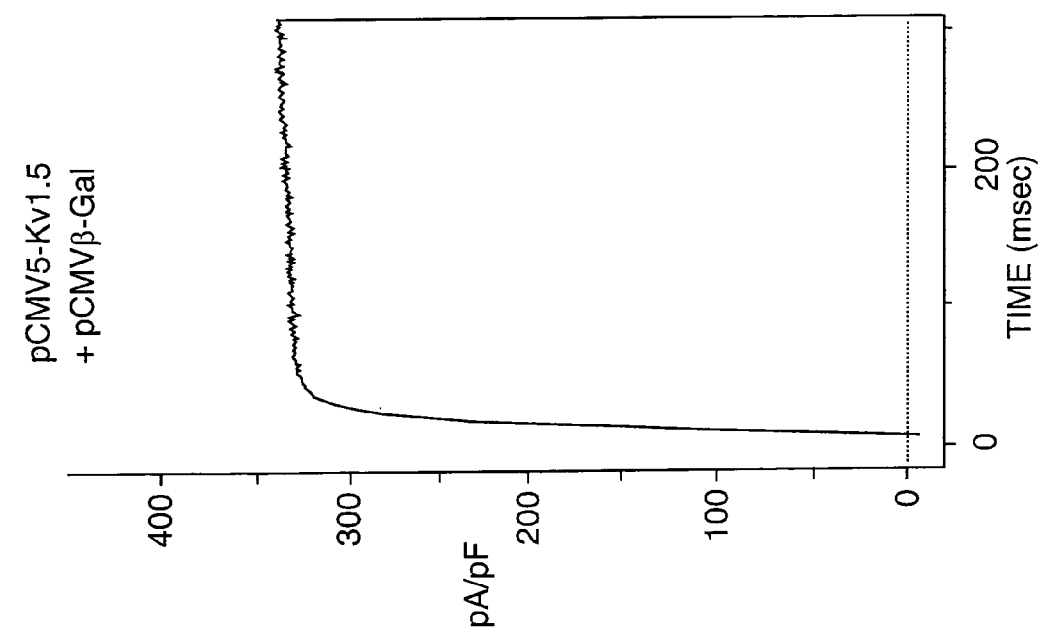

FIGS. 9A–F are explained as follows. Wild type Kv4.2 currents expressed in CHO-K1 cells co-transfected with pCMVβ-Gal (FIG. 9A) or pE1Kv4.2ST (FIG. 9B), currents were elicited at +40 mV. Summary data for peak current densities (FIG. 9C) were obtained by subtracting the prepulse inactivated current (0 mV prepulse) from the fully primed current (−90 mV prepulse). The magnitude of Kv1.5 current expressed in CHO-K1 cells is not affected by cotransfection with Kv4.2ST (FIG. 9D vs. FIG. 9E). The mean data shown in (FIG. 9F) summarizes the results of 5+6 experiments.

EXAMPLE 7

Somatic Cell Gene Transfer of Modified Potassium Current Genes

Isolation of Cerebellar Granule Cells—Cerebellar granule cells were isolated as previously described Levi, G., et al. (1989) *Manual of the Nervous System* pp. 211. Cells were plated on dishes that had been coated with poly-L-lysine (5 ug/ml for 10 minutes). If coverslips were needed they were sterilized by immersion in 95% EtOH followed by flaming in a bunsen burner. Coverslips were then placed in the dishes prior to coating with poly-lysine. Cells were cultured in Basal Eagle's medium with Earle's salts free of glutamine (Life Technologies Inc., Gaithersburg, Md.) that had been supplemented with 10% heat inactivated (HI) FBS, 100 μg/ml gentamicin, 25 mM KCl, and 2 mM L-glutamine. The media was removed after one day and replaced with fresh media containing 10 uM cytosine arabinoside (AraC). Under these culture conditions, expression of the A-type current is stable throughout the course of the experiment Gorter, J. A., et al. (1995) *J. Neurophysiol.* 74:298.

Isolation of Ventricular myocyte cells— Adult rat ventricular myocytes were isolated by enzymatic dissociation as previously described Hilal-Dandan, R., et al. (1991) *J. Mol. Cell Cardiol.* 23:705. Cells were cultured on laminin-coated coverslips in Medium 199 with Earles salts and L-glutamine (CellGro, Mediatech, Washington D.C.) supplemented with penicillin, streptomycin, and 4% fetal bovine serum (LifeTechnologies, Gaithersburg, Md.).

Cultured rat cerebellar granule cells were co-infected with a 3:1 ratio of Ad4.2ST or Adβ-Gal: AdhGFP, on day three in culture. The multiplicity of infection (m.o.i.) which gave best results was in the range of 100 to 500. The AdhGFP allowed visual inspection of the percent infected cells. Infections were carried out in a minimal volume of culture media supplemented with HI 2% FBS for two hours at 37° C. The best results were obtained by removing a cover slip of cells from the dish and placing it into a fresh dish where it was covered with 100 to 200 μl of infection media. Surface tension was sufficient to hold the infection media in place. Following the 2 hour infection time the coverslip was placed back in the original culture plate and monitored for the appearance of GFP in granule cells (24–48 hrs.). If the cells had been co-infected with β-galactosidase they were further processed by fixing in 4% paraformaldehyde and stained for β-galactosidase activity.

Cerebellar granule neurons were chosen to test the idea that the A-type current is encoded by Shal family genes (Serodio, P., et al. (1996) *J. Neurophys.* 75:2174; Gorter, J. A., et al. (1995) *J. Neurophysiol.* 74:298; Zegarra-Moran, O., et al. (1994) *Exp. Brain Res.* 98:298). In addition, these cells are easily maintained in culture with minimal changes in A-type current density over time. Infection of cultures of granule neurons using low m.o.i.'s (10–50) of AdhGFP resulted primarily in infection of surrounding glial cells, as had been previously observed in other neuronal cultures Moriyoshi, K., et al. (1996) *Neuron* 16:255. Granule cells are easily distinguished from glial cells by their size and morphology. When moi's were increased to 100–500, infection of neuronal cells could be observed at 24 to 48 hours. To positively identify infected neurons for electrophysiologic study, AdhGFP was included in all infections and the duration of expression was calculated from the first appearance of GFP-positive neurons.

Rat ventricular myocytes were similarly infected except that the m.o.i.'s used were in the range of 5 to 20 and it was not necessary to infect a single coverslip at a time as there were no surrounding cells as with neuronal culture. Admt-GFP was used to monitor infection efficiency for myocytes rather than AdhGFP.

Rat ventricular myocytes were also chosen due to the established presence of both Kv4.2 and Kv4.3 mRNA in the heart, and the relative ease with which these cells could be maintained for several days in primary culture Dixon, J. E., et al. (1994) *Circ. Res.* 75:252; Dixon, J. E., et al. (1996) *Circ. Res.* 79:659.

EXAMPLE 7

Electrophysiology of Constructs Expressing the Kv4.2 ST Potassium Channel Gene

The following experiments verify that Kv4.2 ST works as designed in transient cotransfection experiments with functional Kv4.2.

Experiments were performed at 21–23° C. Whole-cell currents were recorded with Axopatch 200A amplifier (Axon Instruments, Foster City, Calif.) sampled at 10 kHz and filtered at 1–5 kHz. The pipette solution contained (in mM) 140 KCl, 1 $MgCl_2$, 5 EGTA, 4 MgATP, 10 HEPES (pH 7.2). The use of intracellular EGTA suppressed any calcium-dependent component of the transient outward current Zygmunt, A. C., et al. (1991) *Circulation Research* 68:424, which might have been present in the rat ventricular myocytes; the remaining $I_{to}$ thus consists entirely of the calcium-independent transient outward potassium current (also called $I_{to\,1}$). The bath solution contained (in mM) 140 NaCl, 5.4 KCl, 2 $CaCl_2$, 1 $MgCl_2$, 10 glucose, 10 HEPES (pH 7.4). For comparison between groups, peak currents are normalized for cell size based on the capacitance of the cell and expressed as current density (pA/pF).

To reduce experimental variability in cotransfections, cells were routinely studied between 42 and 50 hours after the introduction of the transgene. Viral infections of primary cells were also studied at this time, for consistency with the cotransfection and for the following practical reasons. In the case of adult cardiac myocytes, variable changes in ion channel expression with increasing time in culture were too great to allow statistical evaluation beyond 2–3 days. The cerebellar granule neurons began to exhibit cytopathic effects at time points past 72 hours of infection in both control and test infections.

FIGS. 10A–B show current density in controls (10B) and in Kv4.2 ST-cotransfected CHO cells (10A). Cotransfection of Kv4.2 ST prevented the expression of functional channels.

Figure 11A:
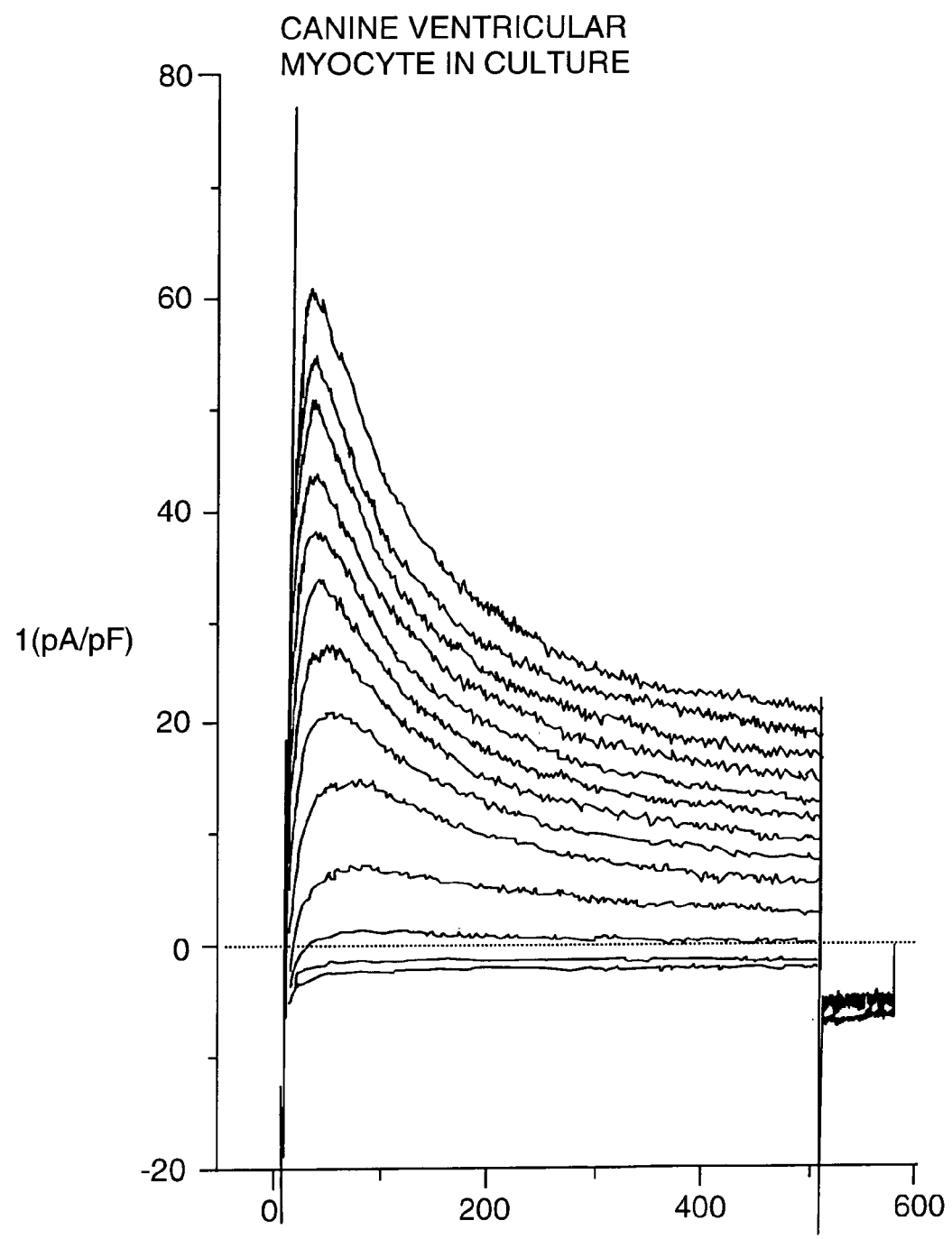
FIGS. 11A–B are graphs showing whole-currents of Ad-KV4.XST in canine ventricular myocytes.
Figure 11B:
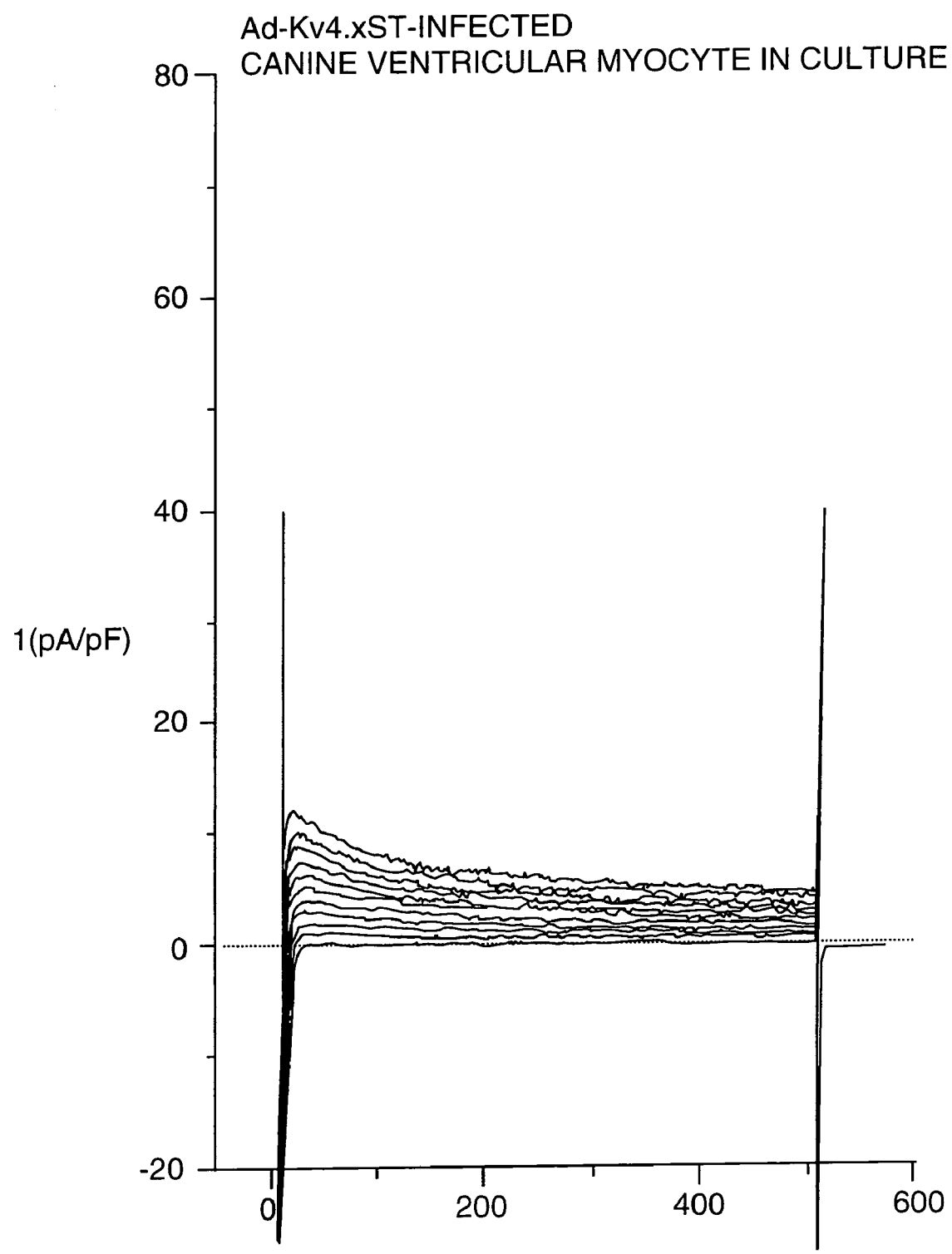

Using the somatic cell gene transfer protocol disclosed above, heart cells were infected (canine ventricular myocytes) with AdKv4.2ST. It was found that the transient outward current was eliminated (FIGS. 11A–B). The effect was selective for the transient outward current. The Kv4 gene family has been proposed to underlie the transient outward current, although this had never been demonstrated using a dominant negative approach. Thus, this verifies that truncated channel genes can be used to knock out endogenous currents in mammalian heart cells. The approach can thus be used to predict the functional consequences of a drug designed to suppress the transient outward current.

FIG. 12A shows representative A-type currents elicited in an Adβ-Gal-infected control cell upon depolarization to +40 mV following prepulses to two different potentials (−90 mV, −40 mV, 500 mS). Infection with AdKv4.2ST suppresses the A-type current in the cerebellar granule neurons, without affecting the maintained component (FIG. 12B). The pooled data from 8 control and 8 test cells (FIG. 12C) confirm that the reduction in current density by AdKv4.2ST is significant (p<0.001). The virally-mediated suppression of native A-type current in neurons is not complete at 42 to 50 hours, unlike the suppression of the expressed Kv4.2 current (FIGS. 9A–F). The remaining transient currents decay at the same rate as the control currents, suggesting that the residual current is comprised of channels that are functionally identical to those which were knocked out. Thus, the lack of complete knockout likely reflects competition between the time course of expression of the Kv4.2ST gene product and the turnover rate of the functional channel subunits. Alternatively, it is possible that other, non-Kv4 family genes encode a minor fraction of the A-type current.

FIGS. 12A–C are explained as follows. Cerebellar granule neurons infected with AdCMVβ-Gal (FIG. 12A) exhibit large transient and maintained outward currents upon depolarization to +40 mV. The transient component of current can be inactivated with a pre-pulse to −40 mV. AdKv4.2ST infection (FIG. 12B) results in a marked suppression of the transient component without affecting the maintained component of outward current. Results of 8 experiments are summarized in FIG. 12C. FIGS. 12A–C show that AdKv4.2ST suppresses the A-type current of cerebellar granule neurons.

Figures 13A, 13B, 13C:
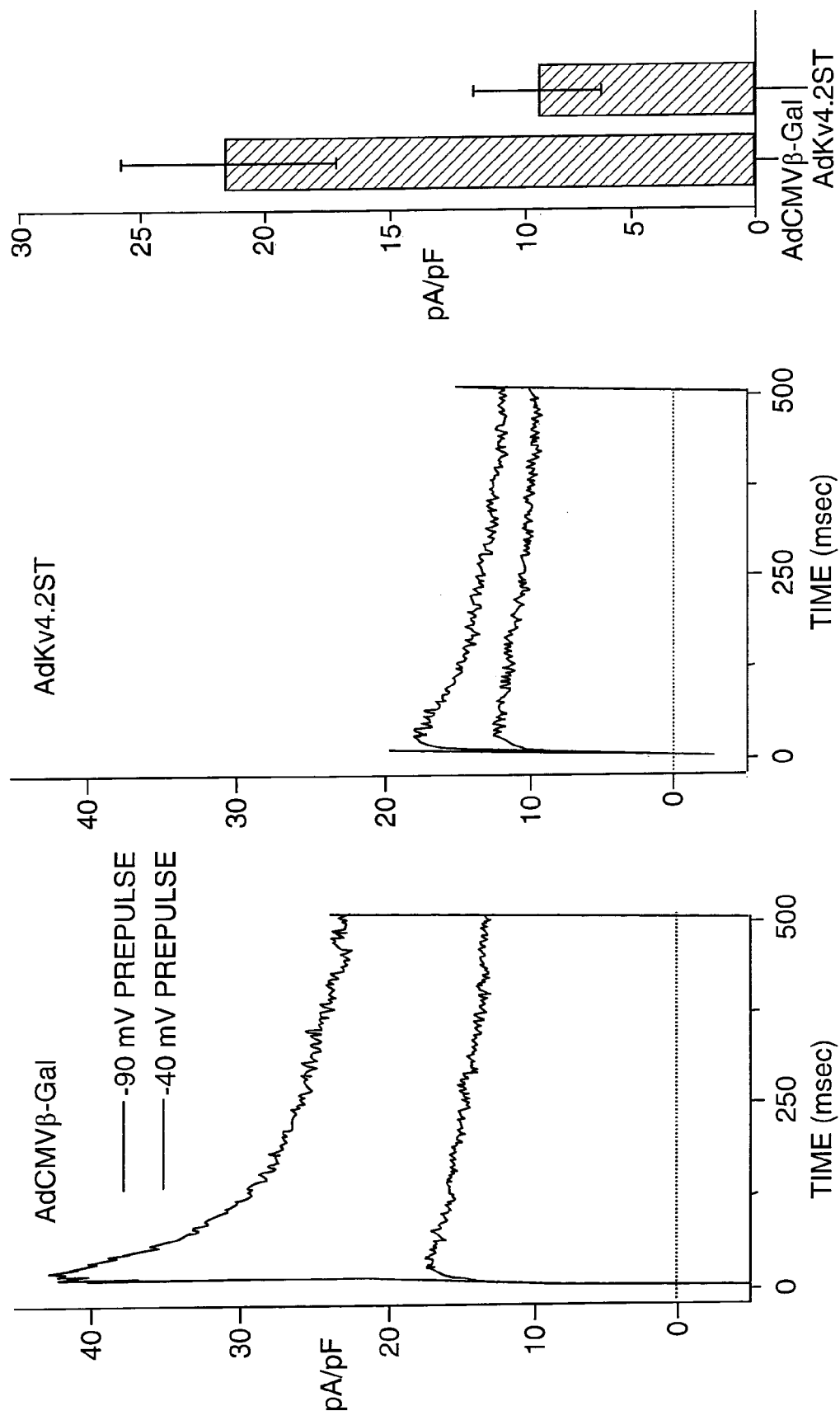
FIGS. 13A–C are graphs depicting suppression of $I_{to\ 1}$ by AdKv4.2ST in adult rat ventricular myocytes.

FIGS. 13A–C show the fully primed and pre-pulse inactivated (−90 mV, −40 mV) transient outward currents elicited by test pulses to +40 mV in a myocyte infected with Adβgal (FIG. 13A) and in another infected with AdKv4.2ST (FIG. 13B). The pooled data in FIG. 13C (N=6 in each group) confirm the significant suppression of native rat cardiac $I_{to}$ by infection with AdKv4.2ST. As was the case with the cerebellar granule cells, the suppression of current was substantial but not complete at 42 to 50 hours. Nevertheless, the results indicate that Kv4 genes constitute the major contributors to $I_{to}$ in heart cells and to A-type currents in cerebellar granule cells.

FIGS. 13A–C are described as follows. $Ca^{2+}$-independent transient outward currents at +40 mV recorded in AdCMVβ-Gal infected myocytes are compared to currents in AdKv4.2ST infected myocytes (FIG. 13B). Peak $I_{to}$ current was measured as the difference between pre-pulse inactivated (0 mV) and fully primed currents. A marked suppression in the peak current density is indicated in the summary data (FIG. 13C). FIGS. 13A–C illustrate that AdKv4.2ST suppresses $I_{to\,1}$ in adult rat ventricular myocytes.

EXAMPLE 8

Analysis of Constructs Encoding Fused Kv4.2-GFP Fusion Proteins

Electrophysiology—To probe the mechanism of action of Kv4.2ST, fusion constructs were generated with enhanced green fluorescent protein (EGFP) so that the expressed truncated protein could be localized within living cells with confocal imaging. We first confirmed that the fusion protein GFP-Kv4.2ST acted similarly to Kv4.2ST (FIGS. 14A–I).

FIGS. 14A and 14B show currents recorded in a CHO-K1 cell co-transfected with pRCCMVKv1.4 and pCMVβ-Gal (FIG. 14A) or pGFPKv4.2ST (FIG. 14B). As was the case for Kv4.2ST and Kv1.5, there is no suppression of Kv1.4 by GFP-Kv4.2 (FIG. 14C). Nevertheless, the fusion protein could suppress Shal family currents (either Kv4.2, FIG. 14 D–F, or Kv4.3, FIGS. 14 G–I). The summary data in FIGS. 14 F and I show comparable levels of suppression for Kv4.2 and Kv4.3 (P≦0.005). Kir2.1-AAA is an unrelated inwardly rectifying potassium channel with a pore mutation designed to suppress Kir2.1 channels Tinker, A., et al. (1996) *Cell* 87:857, and was added as a control in these experiments to ensure that suppression of Kv4.2 current was not simply attributable to co-expression with another membrane protein. This control is particularly apt because GFPKir2.1-AAA does suppress the functional expression of inwardly rectifying currents encoded by wild-type Kir2.1, Schreur, K., et al. (1997) *Circulation* 96:1–422.

Figures 14D, 14E, 14F:
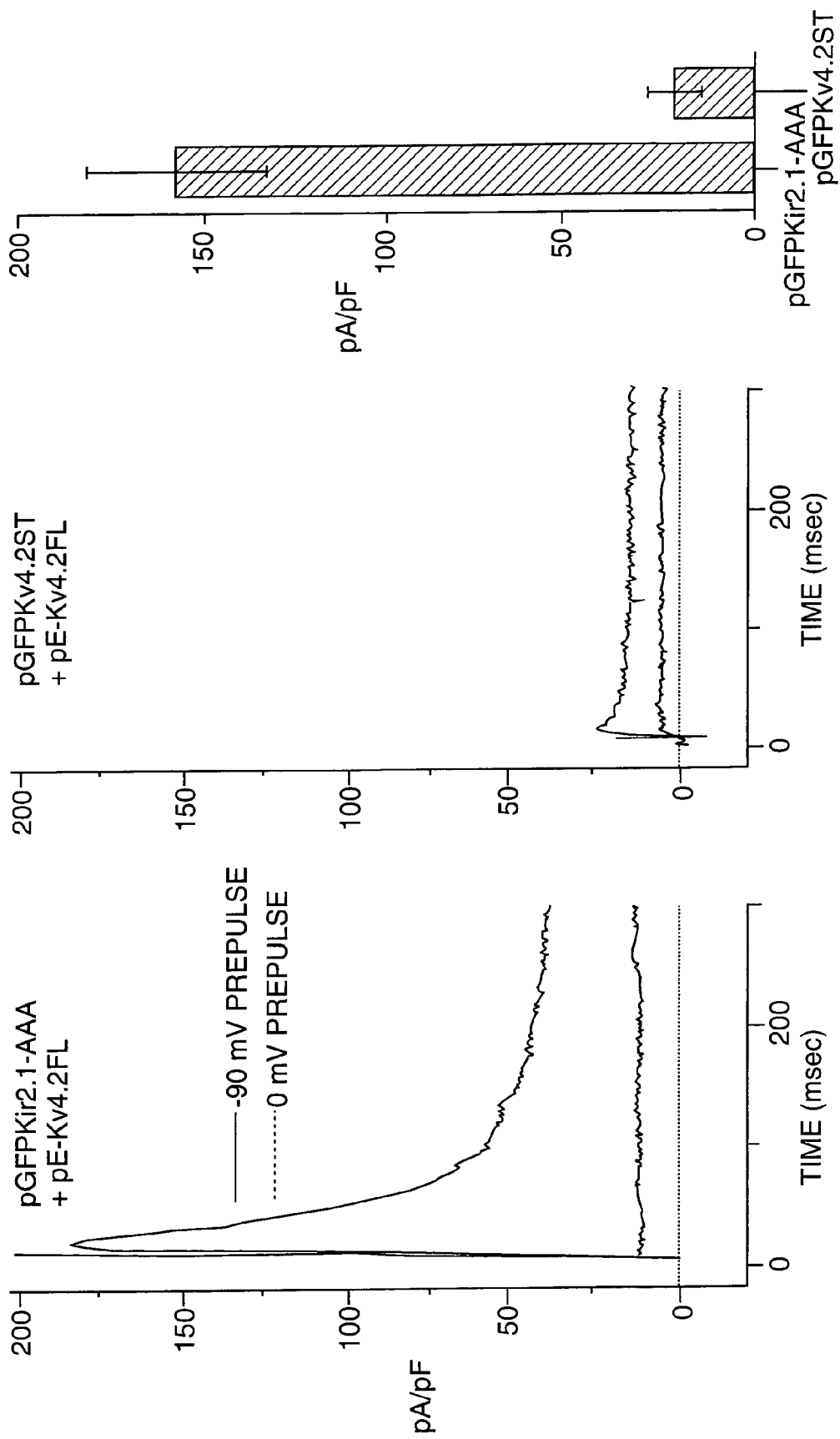
Figures 14G, 14H, 14I:
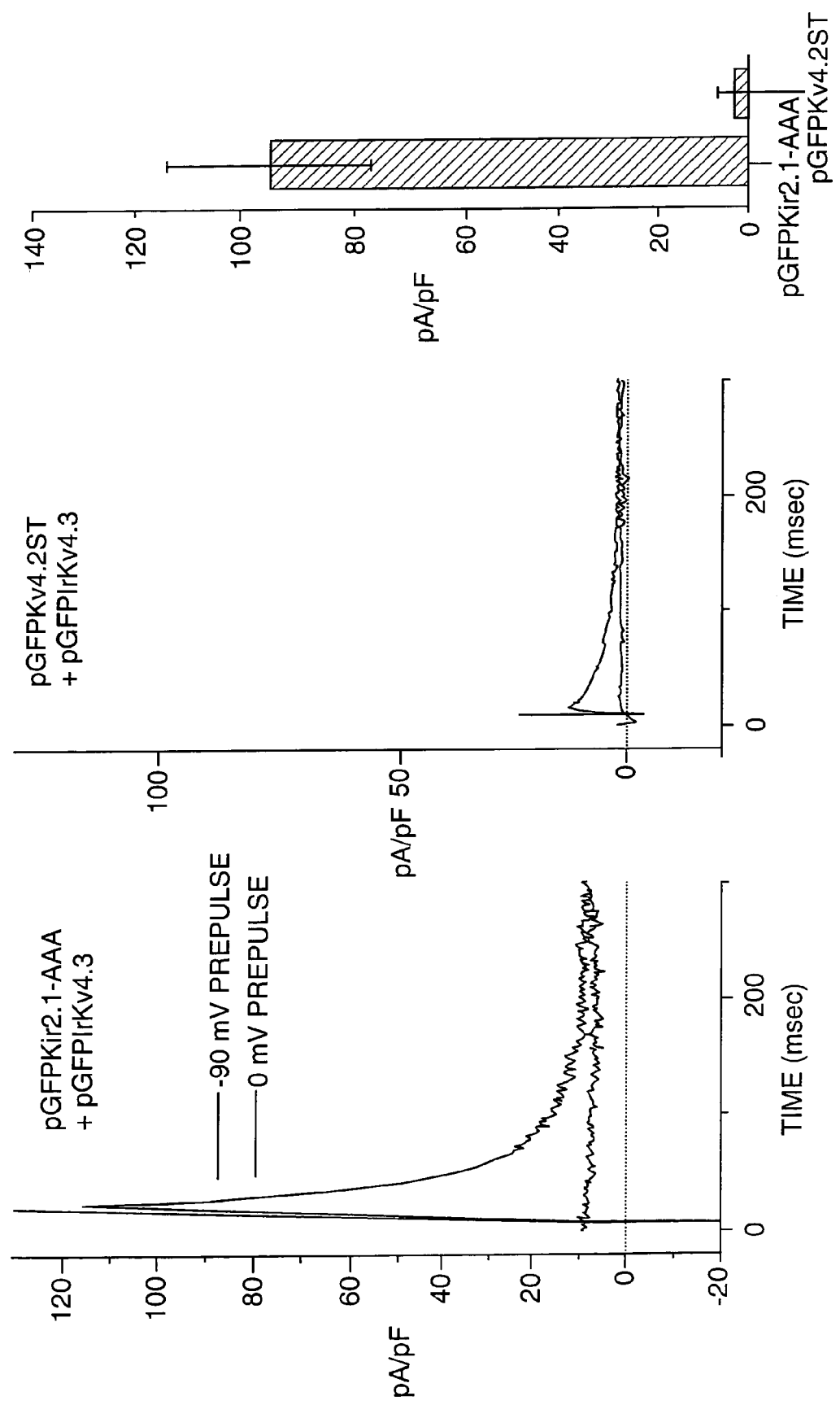

FIGS. 14A–I are explained as follows. Currents recorded from CHO-K1 cells co-transfected with pRC-CMVKv1.4 and pCMVβ-Gal (FIG. 14 A) or pGFP-Kv4.2ST (FIG. 14B) are not significantly different (n=5)(FIG. 14C). Wild type Kv4.2 currents from CHO-K1cells co-transfected with a dominant negative construct for Kir2.1 (pGFPKir2.1-AAA) (FIG. 14D) are compared to currents in cells co-transfected with pGFP-Kv4.2ST (FIG. 14E). The fusion construct containing Kv4.2ST causes a large reduction in average current density (n=3) (FIG. 14F). This effect is mimiced when a Kv4.3 expression vector (pGFPIrKv4.3) is used in place of pE-Kv4.2FL (FIGS. 14G, H). The reduction in Kv4.3 current achieved by GFP-Kv4.2ST in four experiments is significant (FIG. 14I). FIGS. 14A–I show that a modified Kv4.2ST (GFP-Kv4.2ST) also specifically suppresses Shal family currents.

Confocal Microscopy—CHO-K1 cells (CCL-61 American Type Culture Collection, Rockville, Md.) plated on glass coverslips were transfected with pGFP-Kv4.2ST or with pGFP-Kv4.2ST and pE-Kv4.2FL using Lipofectamine. After 36 hours cells were washed with PBS and placed upside down on a microscope slide over a drop of PBS. The edges of the coverslip were sealed with rubber cement to prevent drying. Images were taken on a laser scanning confocal microscope (PCM 2000, Nikon Inc., Melville, N.Y., EX 488, EM 505–530) with a 60× objective lens (NA 1.2).

Confocal imaging of CHO-K1 cells transfected with pGFP-Kv4.2ST (FIG. 15A) or cotransfected with pGFP-Kv4.2ST and pE-Kv4.2FL (FIG. 15B) reveals that the fusion construct is richly concentrated in the perinuclear region of the cells. In families of Z-plane images fluorescence intensity was also detected on the surface of the cells. These findings suggest that, at least some of the suppression of functional current may be due to premature degradation of heteromeric channel complexes, and/or to effects on the processing of the mature protein prior to externalization. However, this apparently abnormal localization of a membrane protein does not seem to be restricted to the truncated version of this protein, as fusion constructs containing full-length channels also have similar localization patterns despite the fact that robust membrane currents can be readily detected in such cells (Marshall, J. et al. (1995) *Neuron* 14:211). Therefore, it is not possible at this time to state unequivocally whether the suppression of current occurs as a result of premature degradation, as the result of the formation of non-functional tetramers in the surface membrane, or as a combination of the two effects.

Figure 15B:
FIGS. 15A–B are confocal photomicrographs illustrating GFP-Kv4.2ST protein distributed in various cell membranes.
Figure 15A:
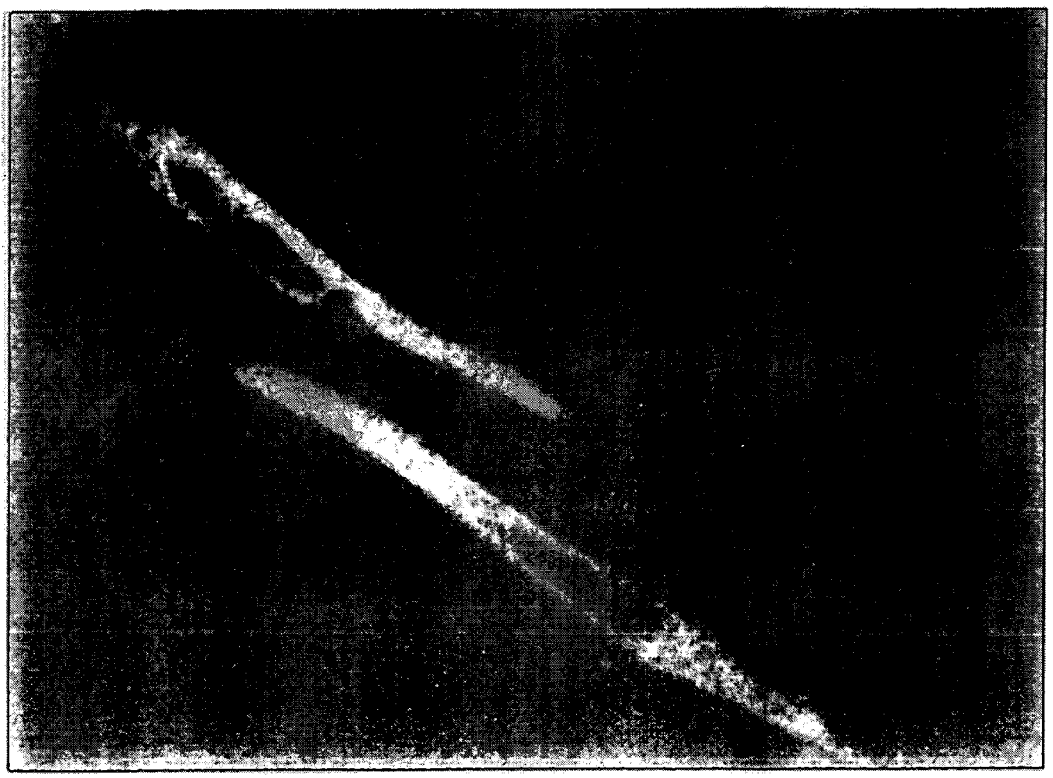

FIGS. 15A and B are explained as follows. A confocal image of pGFP-Kv4.2ST transfected into CHO-K1 cells (FIG. 15A) shows concentration of the fusion protein in the intracellular membranes. This distribution is similar in a cell that was cotransfected with pGFP-Kv4.2ST and pE-Kv4.2FL (FIG. 15B). FIGS. 15A and 15B show that GFP-Kv4.2ST is distributed in various cell membranes.

The examples shown above demonstrate use of a dominant negative Kv4.2 ion channel construct that specifically suppresses the transient outward current of rat ventricular myocytes as well as the A-type current of cerebellar granule neurons. These two cell types have previously been shown by other methods to express Kv4 family genes. See Dixon, J. E., et al. (1994) *Circ. Res.* 75:252; Barry, D. M., et al. (1995) *Circ. Res.* 77:361; Dixon, J. E., et al. (1996) *Circ. Res.* 79:659; Serodio, P., et al. (1996) *J. Neurophys.* 75:2174; Maletic-Savatic, M., et al. (1995) *J. Neurosci* 15:3840; Fiset, C., et al. (1997) *Journal of Physiology* 500:51.

It is shown that Kv4.2ST specifically suppresses members of the Shal family. It is believed that this is the first experimental demonstration that Shal family members can form heteromultimers with each other. This strategy provides a unique way of determining the molecular identity of macroscopic ionic currents in native cells and may provide a useful tool in understanding the exact role these currents play in cellular physiology. The use of the adenovirus vector also allows the potential use of this strategy in-vivo as well as in-vitro. While the introduction of dominant negative constructs may also be achieved by transgenic approaches, developmental adaptation or possible lethal effects may complicate the interpretation of such experiments.

Some of the examples employs disclosed above use statistical analysis to present data. Statistical analyses were achieved by pooling relevant data as the mean± the standard error of the mean (s.e.). Comparisons of means between groups were performed using one way ANOVA. P values less then 0.05 were deemed significant.

The following abbreviations were used in the text: $I_{to}$ and $I_A$, transient outward current; CMV, cytomegalovirus; RSV, rous sarcoma virus; LTR, long terminal repeat; IRES, internal ribosome entry site; m.o.i., multiplicity of infection; EGFP, enhanced green fluorescent protein; AraC, cytosine arabinoside, β-gal, *Escherichia coli* lacZ gene; pF, picofarad.

The invention has been described with reference to preferred embodiments thereof. However, it will be appreciated that those skilled in the art, upon consideration of this disclosure, may make modifications and improvements within the spirit and scope of the invention.

The invention claimed is:

1. A method for predicting the pharmacological effect a drug candidate compound would have in a cell, tissue, or organ that expresses a protein, comprising:
   a) modulating, by somatic gene transfer, expression of the protein in host cells;
   b) comparing the phenotype of the host cells in which expression of the protein has been modulated to the phenotype of control host cells in which expression of the protein has not been modulated; and
   c) analyzing the result of expression of the protein by correlating the result of expression of the modified protein to the result of expression of a corresponding native protein,
   wherein a result of expression of the protein whose expression modulated in step (a) mimics one or more of the effects of the drug candidate compound, and
   wherein the phenotype is propagation of an electrical charge, pattern of electrical signaling, contraction, growth, blebbing or budding, pycnotic transformation, kinesis, cell death, differentiation, replication, transcription, translation, protein processing, adhesion, oncogenetic transformation, enzymatic catalysis, or functional modification.

2. The method of claim 1, wherein the protein is a drug target protein.

3. The method of claim 1, wherein the difference in phenotype between the host cells in which expression of the protein has been modulated and the phenotype of control host cells in which expression of the protein has not been modulated comprises an alteration in a function of the cells.

4. The method of claim 1, wherein the difference in phenotype between the host cells in which expression of the protein has been modulated and the phenotype of control host cells in which expression of the protein has not been modulated comprises suppression of a function of the cells.

5. The method of claim 1, wherein the difference in phenotype between the host cells in which expression of the protein has been modulated and the phenotype of control host cells in which expression of the protein has not been modulated comprises induction of a function of the cells.

6. The method of claim 1, wherein expression of the protein is increased following the somatic gene transfer.

7. The method of claim 6, wherein the increase in expression is achieved by operably linking a gene encoding the protein to an inducible or viral promoter.

8. The method of claim 1, wherein expression of the protein is inhibited following the somatic gene transfer.

9. The method of claim 8, wherein expression of the protein is inhibited by transfer of a gene truncated relative to a corresponding native gene.

10. The method of claim 9, wherein the truncation is a contiguous or non-contiguous deletion of the transferred gene.

11. The method of claim 10, wherein expression of the protein is inhibited by transfer of a gene encoding one or more amino acid substitutions relative to a corresponding native protein.

12. The method of claim 1, wherein the protein is capable of specifically forming a binding complex with at least one other protein molecule.

13. The method of claim 12, wherein expression of the protein is sufficient to produce a dominant negative mutation that reduces or blocks function of the binding complex.

14. The method of claim 1, further comprising screening the potential drug target protein using natural products testing, synthetic chemical testing, combinatory chemistry, targeted diversity, rational drug design, or selective gene suppression techniques.

15. The method of claim 1, wherein the phenotype is propagation of an electrical charge.

16. The method of claim 1, wherein the phenotype is cell growth.

17. The method of claim 1, wherein the phenotype is blebbing or budding.

18. The method of claim 1, wherein the phenotype is pycnotic transformation.

19. The method of claim 1, wherein the phenotype is kinesis.

20. The method of claim 1, wherein the phenotype is cell death.

21. The method of claim 1, wherein the phenotype is cell differentiation.

22. The method of claim 1, wherein the phenotype is cell replication.

23. The method of claim 1, wherein the phenotype is transcription or translation.

24. The method of claim 1, wherein the phenotype is protein processing.

25. The method of claim 1, wherein the phenotype is protein adhesion.

26. The method of claim 1, wherein the phenotype is oncogenetic transformation.

27. The method of claim 1, wherein the phenotype is enzymatic catalysis.

28. The method of claim 1, wherein the phenotype is protein modification.

29. The method of claim 1, wherein the phenotype is pattern of electrical signaling.

30. The method of claim 1, wherein the phenotype is contraction.

31. The method of claim 1, wherein the phenotype is cell growth.

32. The method of claim 1, wherein the phenotype is functional modification.

* * * * *

SEQUENCE LISTING

<160> NUMBER OF SEQ ID NOS: 2

<210> SEQ ID NO 1
<211> LENGTH: 630
<212> TYPE: PRT
<213> ORGANISM: Unknown Organism
<220> FEATURE:
<223> OTHER INFORMATION: Description of Unknown Organism: Mammalian ion
      channel protein

<400> SEQUENCE: 1

Met Ala Ala Gly Val Ala Ala Trp Leu Pro Phe Ala Arg Ala Ala Ala
 1               5                  10                  15

Ile Gly Trp Met Pro Val Ala Ser Gly Pro Met Pro Ala Pro Pro Arg
                20                  25                  30

Gln Glu Arg Lys Arg Thr Gln Asp Ala Leu Ile Val Leu Asn Val Ser
            35                  40                  45

Gly Thr Arg Phe Gln Thr Trp Gln Asp Thr Leu Glu Arg Tyr Pro Asp
        50                  55                  60

Thr Leu Leu Gly Ser Ser Glu Arg Asp Phe Phe Tyr His Pro Glu Thr
    65                  70                  75                  80

Gln Gln Tyr Phe Phe Asp Arg Asp Pro Asp Ile Phe Arg His Ile Leu
                85                  90                  95

-continued

```
Asn Phe Tyr Arg Thr Gly Lys Leu His Tyr Pro Arg His Glu Cys Ile
            100                 105                 110
Ser Ala Tyr Asp Glu Glu Leu Ala Phe Phe Gly Leu Ile Pro Glu Ile
            115                 120                 125
Ile Gly Asp Cys Cys Tyr Glu Glu Tyr Lys Asp Arg Arg Arg Glu Asn
130             135                 140
Ala Glu Arg Leu Gln Asp Asp Ala Asp Thr Asp Asn Thr Gly Glu Ser
145                 150                 155                 160
Ala Leu Pro Thr Met Thr Ala Arg Gln Arg Val Trp Arg Ala Phe Glu
                165                 170                 175
Asn Pro His Thr Ser Thr Met Ala Leu Val Phe Tyr Tyr Val Thr Gly
            180                 185                 190
Phe Phe Ile Ala Val Ser Val Ile Ala Asn Val Val Glu Thr Val Pro
            195                 200                 205
Cys Gly Ser Ser Pro Gly His Ile Lys Glu Leu Pro Cys Gly Glu Arg
            210                 215                 220
Tyr Ala Val Ala Phe Phe Cys Leu Asp Thr Ala Cys Val Met Ile Phe
225                 230                 235                 240
Thr Val Glu Tyr Leu Leu Arg Leu Ala Ala Ala Pro Ser Arg Tyr Arg
                245                 250                 255
Phe Val Arg Ser Val Met Ser Ile Ile Asp Val Val Ala Ile Leu Pro
            260                 265                 270
Tyr Tyr Ile Gly Leu Val Met Thr Asp Asn Glu Asp Val Ser Gly Ala
            275                 280                 285
Phe Val Thr Leu Arg Val Phe Arg Val Phe Arg Ile Phe Lys Phe Ser
            290                 295                 300
Arg His Ser Gly Gly Leu Arg Ile Leu Gly Tyr Thr Leu Lys Ser Cys
305                 310                 315                 320
Ala Ser Glu Leu Gly Phe Leu Leu Phe Ser Leu Thr Met Ala Ile Ile
                325                 330                 335
Ile Phe Ala Thr Val Met Phe Tyr Ala Glu Lys Gly Ser Ser Ala Ser
            340                 345                 350
Lys Phe Thr Ser Ile Pro Ala Ala Phe Trp Tyr Thr Ile Val Thr Met
            355                 360                 365
Thr Thr Leu Gly Tyr Gly Asp Met Val Pro Lys Thr Ile Ala Gly Lys
            370                 375                 380
Ile Phe Gly Ser Ile Cys Ser Leu Ser Gly Val Leu Val Ile Ala Leu
385                 390                 395                 400
Pro Val Pro Val Ile Val Ser Asn Phe Ser Arg Ile Tyr His Gln Asn
                405                 410                 415
Gln Arg Ala Asp Lys Arg Arg Ala Gln Lys Lys Ala Arg Leu Ala Arg
            420                 425                 430
Ile Arg Ala Ala Lys Ser Gly Ser Ala Asn Ala Tyr Met Gln Ser Lys
            435                 440                 445
Arg Asn Gly Leu Leu Ser Asn Gln Leu Gln Ser Ser Glu Asp Glu Pro
450                 455                 460
Ala Phe Val Ser Lys Ser Gly Ser Ser Phe Glu Thr Gln His His His
465                 470                 475                 480
Leu Leu His Cys Leu Glu Lys Thr Thr Asn His Glu Phe Val Asp Glu
                485                 490                 495
Gln Val Phe Glu Glu Ser Cys Met Glu Val Ala Thr Val Asn Arg Pro
            500                 505                 510
```

```
Ser Ser His Ser Pro Ser Leu Ser Ser Gln Gln Gly Val Thr Ser Thr
        515                 520                 525

Cys Cys Ser Arg Arg His Lys Lys Thr Phe Arg Ile Pro Asn Ala Asn
        530                 535                 540

Val Ser Gly Ser His Arg Gly Ser Val Gln Glu Leu Ser Thr Ile Gln
545                 550                 555                 560

Ile Arg Cys Val Glu Arg Thr Pro Leu Ser Asn Ser Arg Ser Ser Leu
                565                 570                 575

Asn Ala Lys Met Glu Glu Cys Val Lys Leu Asn Cys Glu Gln Pro Tyr
                580                 585                 590

Val Thr Thr Ala Ile Ile Ser Ile Pro Thr Pro Pro Val Thr Thr Pro
                595                 600                 605

Glu Gly Asp Asp Arg Pro Glu Ser Pro Glu Tyr Ser Gly Gly Asn Ile
            610                 615                 620

Val Arg Val Ser Ala Leu
625                 630

<210> SEQ ID NO 2
<211> LENGTH: 214
<212> TYPE: PRT
<213> ORGANISM: Unknown Organism
<220> FEATURE:
<223> OTHER INFORMATION: Description of Unknown Organism: Mammalian ion
      channel protein

<400> SEQUENCE: 2

Met Ala Ala Gly Val Ala Ala Trp Leu Pro Phe Ala Arg Ala Ala Ala
  1               5                  10                  15

Ile Gly Trp Met Pro Val Ala Ser Gly Pro Met Pro Ala Pro Pro Arg
                20                  25                  30

Gln Glu Arg Lys Arg Thr Gln Asp Ala Leu Ile Val Leu Asn Val Ser
            35                  40                  45

Gly Thr Arg Phe Gln Thr Trp Gln Asp Thr Leu Glu Arg Tyr Pro Asp
     50                  55                  60

Thr Leu Leu Gly Ser Ser Glu Arg Asp Phe Phe Tyr His Pro Glu Thr
 65                  70                  75                  80

Gln Gln Tyr Phe Phe Asp Arg Asp Pro Asp Ile Phe Arg His Ile Leu
                85                  90                  95

Asn Phe Tyr Arg Thr Gly Lys Leu His Tyr Pro Arg His Glu Cys Ile
                100                 105                 110

Ser Ala Tyr Asp Glu Glu Leu Ala Phe Phe Gly Leu Ile Pro Glu Ile
            115                 120                 125

Ile Gly Asp Cys Cys Tyr Glu Glu Tyr Lys Asp Arg Arg Arg Glu Asn
    130                 135                 140

Ala Glu Arg Leu Gln Asp Asp Ala Asp Thr Asp Asn Thr Gly Glu Ser
145                 150                 155                 160

Ala Leu Pro Thr Met Thr Ala Arg Gln Arg Val Trp Arg Ala Phe Glu
                165                 170                 175

Asn Pro His Thr Ser Thr Met Ala Leu Val Phe Tyr Tyr Val Thr Gly
            180                 185                 190

Phe Phe Ile Ala Val Ser Val Ile Ala Asn Val Val Glu Thr Gly Ser
        195                 200                 205

Arg His Asp Lys Ile His
    210
```